(12) United States Patent
Nakayama

(10) Patent No.: US 10,584,140 B2
(45) Date of Patent: Mar. 10, 2020

(54) METHOD FOR PRODUCING RUTHENIUM COMPLEX

(71) Applicant: TAKASAGO INTERNATIONAL CORPORATION, Tokyo (JP)

(72) Inventor: Yuji Nakayama, Kanagawa (JP)

(73) Assignee: TAKASAGO INTERNATIONAL CORPORATION, Tokyo (JP)

(*) Notice: Subject to any disclaimer, the term of this patent is extended or adjusted under 35 U.S.C. 154(b) by 0 days.

(21) Appl. No.: 15/764,940

(22) PCT Filed: Sep. 9, 2016

(86) PCT No.: PCT/JP2016/076564
§ 371 (c)(1),
(2) Date: Mar. 30, 2018

(87) PCT Pub. No.: WO2017/056916
PCT Pub. Date: Apr. 6, 2017

(65) Prior Publication Data
US 2018/0273565 A1    Sep. 27, 2018

(30) Foreign Application Priority Data

Sep. 30, 2015    (JP) .................................. 2015-193552

(51) Int. Cl.
*C07F 15/00* (2006.01)
*C07F 19/00* (2006.01)
(Continued)

(52) U.S. Cl.
CPC ......... *C07F 15/0046* (2013.01); *B01J 31/189* (2013.01); *B01J 31/20* (2013.01);
(Continued)

(58) Field of Classification Search
None
See application file for complete search history.

(56) References Cited

U.S. PATENT DOCUMENTS 8,471,048 B2 * 6/2013 Kuriyama ............... C07B 53/00
556/8
2005/0107638 A1   5/2005 Abdur-Rashid
(Continued)

FOREIGN PATENT DOCUMENTS

CN    101730656 A    6/2010
CN    102177170 A    9/2011
(Continued)

OTHER PUBLICATIONS

Wataru Kuriyama et al. "Catalytic Hydrogenation of Esters. Development of an Efficient Catalyst and Processes for Synthesising (R)-1,2-Propanediol and 2-(I-Menthoxy)ethanol" Organic Process Research & Development, 2012, vol. 16, (pp. 166-171).

Richard I. Wingad et al. "Catalytic Conversion of Ethanol to n-Butanol Using Ruthenium P-N Ligand Complexes" American Chemical Society, vol. 5, No. 10, Chart 1, Table 1 (pp. 5822-5826).

Written Opinion (PCT/ISA/237) issued by the International Searching Authority in corresponding International Application No. PCT/JP2016/076564 dated Nov. 1, 2016.

International Search Report (PCT/ISA/210), issued by International Searching Authority in corresponding International Application No. PCT/JP2016/076564, dated Nov. 1, 2016.

(Continued)

*Primary Examiner* — Clinton A Brooks
(74) *Attorney, Agent, or Firm* — Sughrue Mion, PLLC

(57) ABSTRACT

The present invention relates to a method for efficiently producing a ruthenium complex ($1^A$) by reacting a dinuclear ruthenium complex ($2^A$) with a compound ($3^A$) in the presence of a primary alcohol and a base. The ruthenium complex ($1^A$) can also be efficiently produced by treating a dinuclear ruthenium complex ($4^A$) with a primary alcohol and a base. (In the formulas, solid lines, triple lines, broken lines, C, H, N, OP, Ru, X, AH and $R^1$ to $R^{12}$ have the meanings defined in the specification.)

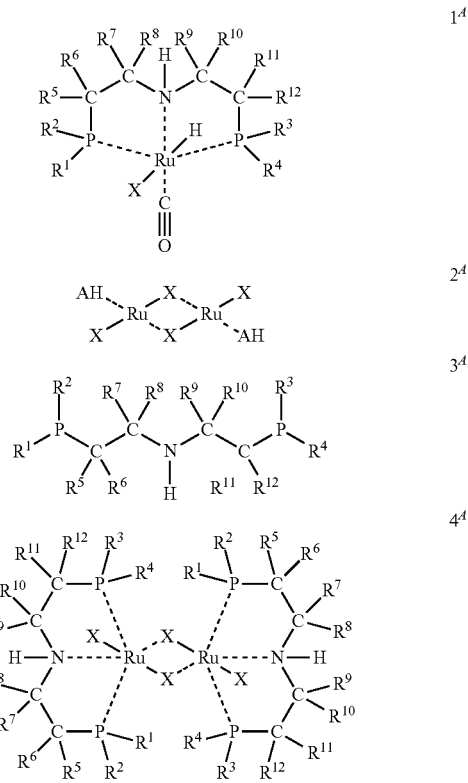

11 Claims, No Drawings

(51) Int. Cl.
*B01J 31/18* (2006.01)
*B01J 31/20* (2006.01)
*B01J 31/24* (2006.01)
*C07F 9/50* (2006.01)
*C07B 61/00* (2006.01)

(52) U.S. Cl.
CPC ....... *B01J 31/2428* (2013.01); *B01J 31/2433* (2013.01); *C07F 19/00* (2013.01); *B01J 2231/643* (2013.01); *B01J 2531/821* (2013.01); *C07B 61/00* (2013.01); *C07B 2200/07* (2013.01); *C07B 2200/09* (2013.01); *C07F 9/50* (2013.01); *C07F 15/00* (2013.01)

(56) References Cited

U.S. PATENT DOCUMENTS

| | | |
|---|---|---|
| 2011/0070152 A1 | 3/2011 | Abdur-Rashid et al. |
| 2011/0237814 A1 | 9/2011 | Kuriyama et al. |
| 2014/0163257 A1 | 6/2014 | Hori et al. |
| 2016/0060195 A1 | 3/2016 | Ding et al. |
| 2016/0288111 A1 | 10/2016 | Dumeignil et al. |
| 2017/0044196 A1 | 2/2017 | Ogata et al. |

FOREIGN PATENT DOCUMENTS

| | | |
|---|---|---|
| CN | 103772142 A | 5/2014 |
| EP | 2 910 540 A1 | 8/2015 |
| JP | 2010527316 A | 8/2010 |
| WO | 2004096735 A2 | 11/2004 |
| WO | 2008/141439 A1 | 11/2008 |
| WO | 2011048727 A1 | 4/2011 |
| WO | 2015/067899 A1 | 5/2015 |
| WO | 2015163440 A1 | 10/2015 |

OTHER PUBLICATIONS

Communication dated Mar. 11, 2019, issued by the European Patent Office in counterpart European Application No. 16851090.7.
Office Action dated Nov. 14, 2019 by the State Intellectual Property Office in counterpart Chinese Patent Application No. 201680057618.9.

* cited by examiner

METHOD FOR PRODUCING RUTHENIUM COMPLEX

TECHNICAL FIELD

The present invention relates to a method for producing [bis(2-phosphinoethyl)amine]carbonylhalohydridoruthenium(II) which is a kind of ruthenium complex exhibiting excellent catalytic activity in a hydrogenation reaction.

BACKGROUND ART

It has been reported that {bis[2-(diphenylphosphino)-ethyl]amine}carbonylchlorohydridoruthenium(II) [Ru-MACHO (registered trademark), hereinafter the same] which is a kind of ruthenium complex exhibits excellent catalytic activity in a hydrogenation reaction of various carbonyl compounds such as ketones, esters and lactones and gives alcohols efficiently (Patent Document 1).

In the production method of this ruthenium complex, as shown in the following reaction formula (Eq. 1), carbonylchlorohydridotris(triphenylphosphine) ruthenium(II) [RuHCl(CO)(PPh$_3$)$_3$] as a ruthenium source and bis[2-(diphenylphosphino)ethyl]amine as a ligand are allowed to react in toluene.

[Chem. 1]

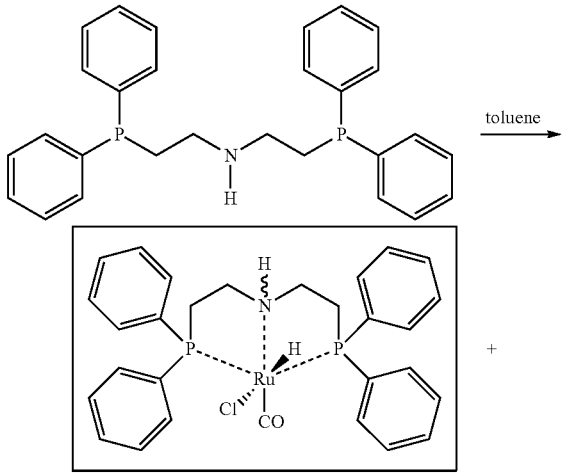

Eq. 1

However, the production method above has a number of problems, for example, that the atom efficiency of the ruthenium source is very low (17.3 mass %) and not only 3 equivalents of difficulty-removable triphenylphosphine (PPh$_3$) are produced as a by-product after the reaction but also the obtained Ru-MACHO is a mixture of isomers (Non-Patent Document 1).

Although Ru-MACHO can be isolated as a single isomer by washing the mixture of isomers with n-hexane and ethanol, this is associated with a problem that the yield decreases from 85% to 55% (Patent Document 1).

PRIOR ART DOCUMENTS

Patent Document

Patent Document 1: WO 2011/048727 A1

Non-Patent Document

Non-Patent Document 1: Wataru Kuriyama, Takaji Matsumoto, Osamu Ogata, Yasunori Ino, Kunimori Aoki, Shigeru Tanaka, Kenya Ishida, Tohru Kobayashi, Noboru Sayo, and Takao Saito, Org. Proc. Res. Dev. 2012, 16, 166-171.

SUMMARY OF THE INVENTION

Technical Problems

Taking into account these circumstances, the present invention has been made. That is, an object of the present invention is to provide a method for simply producing Ru-MACHO and an analogue thereof, which are an excellent catalyst for hydrogenation reaction, as a single isomer in a high yield by using a ruthenium source having excellent atom efficiency without causing production of a difficulty-removable impurity as a by-product.

Solution to Problems

As a result of many intensive studies to attain the above-described object, the present inventors have found that Ru-MACHO is obtained efficiently by reacting dichloro(p-cymene)ruthenium(II) dimer having excellent atom efficiency, as a ruthenium source, with bis[2-(diphenylphosphino)ethyl]amine as a ligand in the presence of a primary alcohol and a base, as shown in the following Eq. 2.

It has also been found that Ru-MACHO is similarly obtained by treating dichloro{[2-(diphenylphosphino)ethyl]amine}ruthenium(II) dimer, which is easily obtained by reacting dichloro(p-cymene)ruthenium(II) dimer with bis[2-(diphenylphosphino)ethyl]amine, with a primary alcohol and a base, as shown in the following Eq. 3.

Simplified outlines of the reactions above are described below using Eq. 2 and Eq. 3, but the present invention is not limited by these outlines.

[Chem. 2]

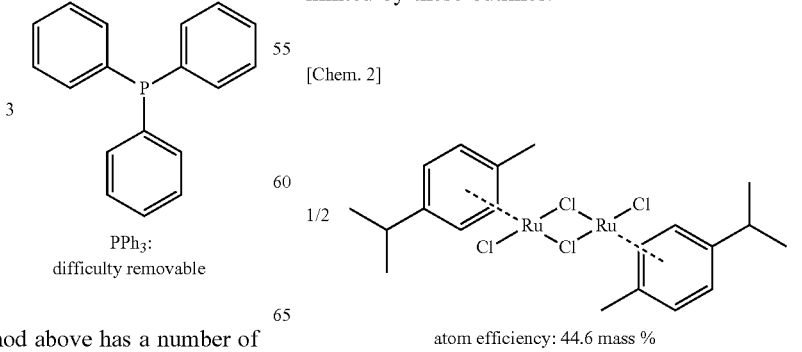

Eq. 2

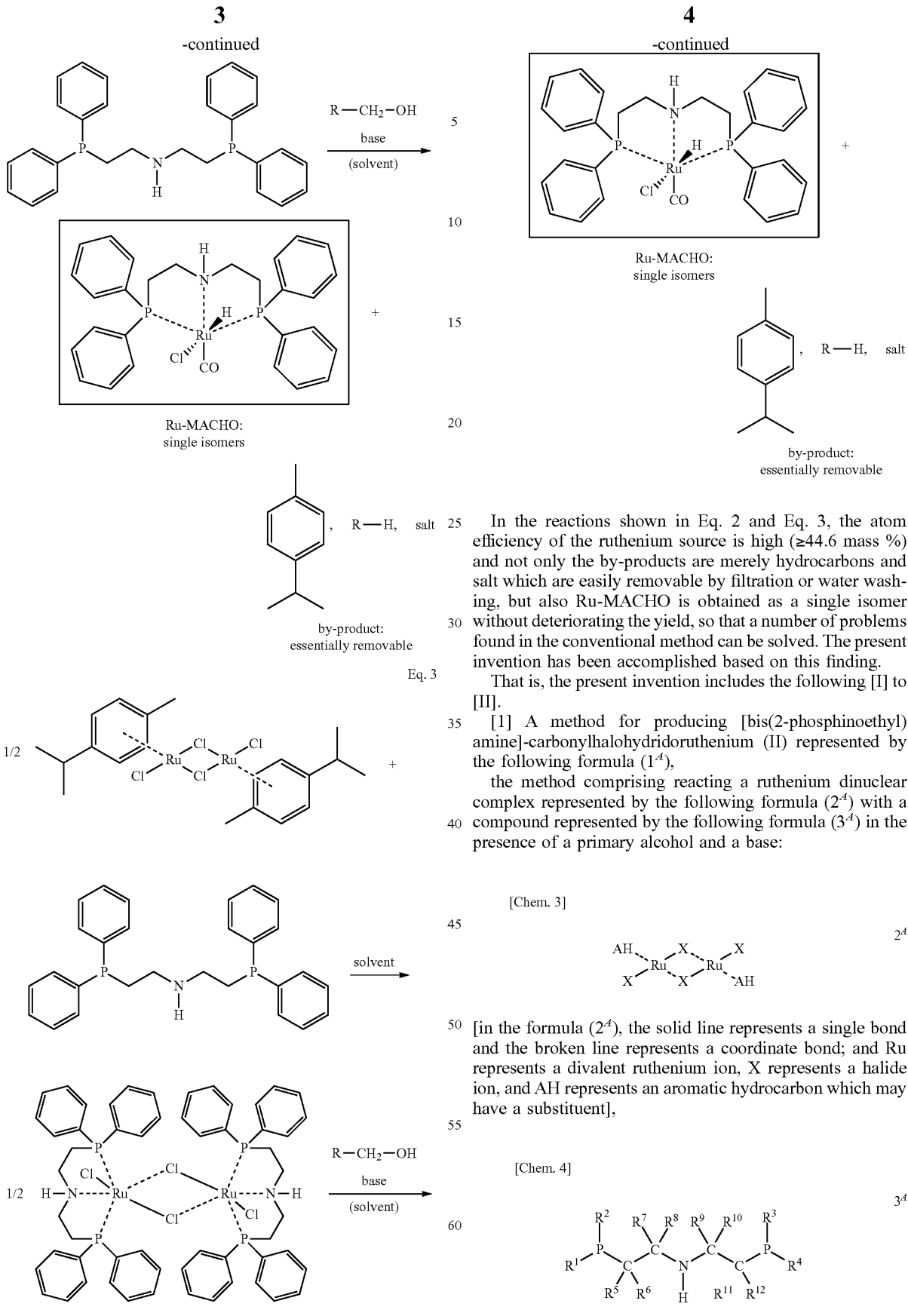

In the reactions shown in Eq. 2 and Eq. 3, the atom efficiency of the ruthenium source is high (≥44.6 mass %) and not only the by-products are merely hydrocarbons and salt which are easily removable by filtration or water washing, but also Ru-MACHO is obtained as a single isomer without deteriorating the yield, so that a number of problems found in the conventional method can be solved. The present invention has been accomplished based on this finding.

That is, the present invention includes the following [I] to [II].

[1] A method for producing [bis(2-phosphinoethyl)amine]-carbonylhalohydridoruthenium (II) represented by the following formula ($1^A$), the method comprising reacting a ruthenium dinuclear complex represented by the following formula ($2^A$) with a compound represented by the following formula ($3^A$) in the presence of a primary alcohol and a base:

[Chem. 3]

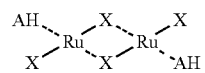

$2^A$

[in the formula ($2^A$), the solid line represents a single bond and the broken line represents a coordinate bond; and Ru represents a divalent ruthenium ion, X represents a halide ion, and AH represents an aromatic hydrocarbon which may have a substituent],

[Chem. 4]

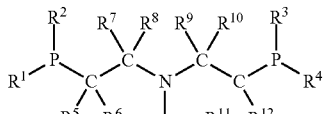

$3^A$

[in the formula ($3^A$), the solid line represents a single bond; C represents a carbon atom, H represents a hydrogen atom, N represents a nitrogen atom, and P represents a phosphorus atom; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^1$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring],

[Chem. 5]

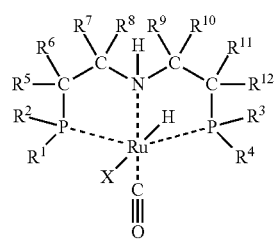

$1^A$

[in the formula ($1^A$), the solid line represents a single bond, the triple line represents a triple bond, and the broken line represents a coordinate bond; C represents a carbon atom, H represents a hydrogen atom, N represents a nitrogen atom, O represents an oxygen atom, and P represents a phosphorus atom; Ru represents a divalent ruthenium ion and X represents a halide ion; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring].

[2] The production method according to [1], wherein the primary alcohol is an alcohol represented by the following formula (5):

[Chem. 6]

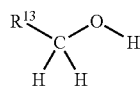

5

[in the formula (5), the solid line represents a single bond; C represents a carbon atom, H represents a hydrogen atom, and O represents an oxygen atom; and $R^{13}$ represents a hydrogen atom or a group selected from the group consisting of an alkyl group which may have a substituent, a cycloalkyl group which may have a substituent, an alkenyl group which may have a substituent, an aryl group which may have a substituent, an oxygen-containing aliphatic heterocyclic group which may have a substituent, and an oxygen-containing heteroaryl group which may have a substituent].

[3] The production method according to [1] or [2], wherein AH is a benzene which may have an alkyl group.

[4] The production method according to any one of [1] to [3], wherein X is a chloride ion.

[5] The production method according to any one of [1] to [4], wherein all of $R^5$, $R^6$, $R^7$, $R^8$, $R^9$, $R^{10}$, $R^{11}$ and $R^{12}$ are a hydrogen atom.

[6] The production method according to any one of [1] to [5], wherein each of $R^1$, $R^2$, $R^3$ and $R^4$ is independently a group selected from the group consisting of an alkyl group, a cycloalkyl group, and an aryl group which may have a substituent.

[7] A method for producing [bis(2-phosphinoethyl)amine]-carbonylhalohydridoruthenium (II) represented by the following formula ($1^A$), the method comprising treating a ruthenium dinuclear complex represented by the following formula ($4^A$) with a primary alcohol and a base:

[Chem. 7]

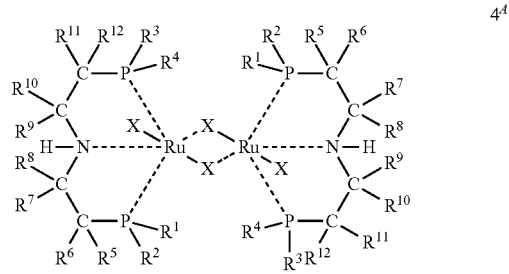

$4^A$

[in the formula ($4^A$), the solid line represents a single bond and the broken line represents a coordinate bond; C represents a carbon atom, H represents a hydrogen atom, N represents a nitrogen atom, and P represents a phosphorus atom: Ru represents a divalent ruthenium ion and X represents a halide ion; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring],

[Chem. 8]

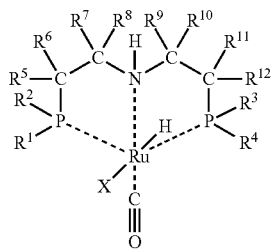

[in the formula (1$^A$), the solid line represents a single bond, the triple line represents a triple bond, and the broken line represents a coordinate bond; C represents a carbon atom, H represents a hydrogen atom, N represents a nitrogen atom, O represents an oxygen atom, and P represents a phosphorus atom; Ru represents a divalent ruthenium ion and X represents a halide ion; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring].

[8] The production method according to [7], wherein the primary alcohol is an alcohol represented by the following formula (5):

[Chem. 9]

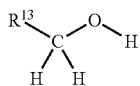

[in the formula (5), the solid line represents a single bond; C represents a carbon atom, H represents a hydrogen atom, and O represents an oxygen atom; and $R^{13}$ represents a hydrogen atom or a group selected from the group consisting of an alkyl group which may have a substituent, a cycloalkyl group which may have a substituent, an alkenyl group which may have a substituent, an aryl group which may have a substituent, an oxygen-containing aliphatic heterocyclic group which may have a substituent, and an oxygen-containing heteroaryl group which may have a substituent].

[9] The production method according to [7] or [8], wherein X is a chloride ion.

[10] The production method according to any one of [7] to [9], wherein all of $R^5$, $R^6$, $R^7$, $R^8$, $R^9$, $R^{10}$, $R^{11}$ and $R^{12}$ are a hydrogen atom.

[11] The production method according to any one of [7] to [10], wherein each of $R^1$, $R^2$, $R^3$ and $R^4$ is independently a group selected from the group consisting of an alkyl group, a cycloalkyl group, and an aryl group which may have a substituent.

Advantageous Effects of the Invention

According to the production method of the present invention, [bis(2-phosphinoethyl)amine]carbonylhalohydridoruthenium(II) represented by the formula (1$^A$) [hereinafter, referred to as the ruthenium complex (1$^A$) of the present invention], examples of which include Ru-MACHO as an excellent catalyst for hydrogenation reaction, can be simply produced as a single isomer in a high yield from a ruthenium dinuclear complex represented by the formula (2$^A$) [hereinafter, referred to as ruthenium dinuclear complex (2$^A$)] as a ruthenium source having excellent atom efficiency and a compound represented by the formula (3$^A$) [hereinafter, referred to as compound (3$^A$)] without causing production of a difficulty-removable impurity as a by-product.

Furthermore, according to the production method of the present invention, similarly, the ruthenium complex (1$^A$) of the present invention can be efficiently produced from a ruthenium dinuclear complex represented by the formula (4$^A$) [hereinafter, referred to as ruthenium dinuclear complex (4$^A$)] which is easily obtained from the ruthenium dinuclear complex (2$^A$) and the compound (3$^A$).

DESCRIPTION OF EMBODIMENTS

The production method of the present invention is described in detail below. First, the ruthenium complex (1$^A$) of the present invention is described. In the formula (1$^A$), the solid line represents a single bond, the triple line represents a triple bond, and the broken line represents a coordinate bond, C represents a carbon atom, H represents a hydrogen atom, N represents a nitrogen atom, O represents an oxygen atom, P represents a phosphorus atom, Ru represents a divalent ruthenium ion, and X represents a halide ion. Specific examples of the halide ion include a fluoride ion, a chloride ion, a bromide ion, and an iodide ion, and preferable specific examples thereof include a chloride ion.

Each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent, and preferably represents an alkyl group, a cycloalkyl group, or an aryl group which may have a substituent.

The alkyl group may be linear or branched, and is, for example, an alkyl group having 1 to 30 carbon atoms, preferably an alkyl group having 1 to 20 carbon atoms, and more preferably an alkyl group having 1 to 10 carbon atoms. Specific examples thereof include a methyl group, an ethyl group, an n-propyl group, a 2-propyl group, an n-butyl group, a 2-butyl group, an isobutyl group, a tert-butyl group, an n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, an n-heptyl group, an n-octyl group, an n-nonyl group, and an n-decyl group.

The cycloalkyl group may be monocyclic or polycyclic, and is, for example, a cycloalkyl group having 3 to 30 carbon atoms, preferably a cycloalkyl group having 3 to 20 carbon atoms, and more preferably a cycloalkyl group having 3 to 10 carbon atoms. Specific examples thereof include a cyclopropyl group, a cyclobutyl group, a cyclopentyl group, a cyclohexyl group, a 1-adamantyl group, and a 2-adamantyl group, and preferable specific examples thereof include a cyclohexyl group.

The alkenyl group may be linear, branched or cyclic, and is, for example, an alkenyl group having 2 to 20 carbon atoms, preferably an alkenyl group having 2 to 14 carbon atoms, and more preferably an alkenyl group having 2 to 8 carbon atoms. Specific examples thereof include a vinyl group, a 1-propenyl group, a 2-propenyl group, an allyl group, a 1-cyclohexenyl group, a 1-styryl group, and a 2-styryl group.

The aryl group is, for example, an aryl group having 6 to 18 carbon atoms, preferably an aryl group having 6 to 14 carbon atoms, and more preferably an aryl group having 6 to 10 carbon atoms. Specific examples thereof include a phenyl group, a 1-naphthyl group, and a 2-naphthyl group, and preferable specific examples thereof include a phenyl group.

The heteroaryl group is, for example, a heteroaryl group derived from a 5- to 6-membered aromatic heterocycle having 1 or 2 heteroatoms selected from the group consisting of an oxygen atom and a sulfur atom, and a heteroaryl group derived from a polycyclic aromatic heterocycle produced by fusion of the aromatic heterocycle with the aryl group above. Specific examples thereof include a 2-furyl group, a 3-furyl group, a 2-thienyl group, a 3-thienyl group, a 2-benzofuryl group, a 3-benzofuryl group, a 2-benzothienyl group, and a 3-benzothienyl group.

The aralkyl group is, for example, a linear or branched aralkyl group formed by substituting at least one hydrogen atom of the alkyl group above with the aryl group above, and a polycyclic aralkyl group formed by fusing the cycloalkyl group above with the aryl group above. Specific examples thereof include a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1-indanyl group, a 2-indanyl group, and a 9-fluorenyl group.

$R^1$ and $R^2$ may be bonded to each other to form a ring which may have a substituent, and $R^3$ and $R^4$ may be bonded to each other to form a ring which may have a substituent. Specific examples of such a ring include a phosphorane ring, a phosphole ring, a phosphinane ring, and a phosphinine ring.

As the substituent that the alkenyl group, aryl group, heteroaryl group and aralkyl group in $R^1$ to $R^4$ and the ring formed by bonding $R^1$ and $R^2$ or bonding $R^3$ and $R^4$ may have, examples thereof include an alkyl group, a cycloalkyl group, a halogenoalkyl group, an alkenyl group, an aryl group, a heteroaryl group, an aralkyl group, an alkoxy group, and a halogeno group. Of these substituents, the alkyl group, cycloalkyl group, alkenyl group, aryl group, heteroaryl group and aralkyl group are the same as the groups described in detail in the description of $R^1$ to $R^4$ above.

The halogenoalkyl group is, for example, a group in which at least one hydrogen atom on the alkyl group above is substituted with a halogen atom. Specific examples thereof include a trifluoromethyl group and an n-nonafluorobutyl group.

The alkoxy group may be linear or branched, and is, for example, an alkoxy group having 1 to 10 carbon atoms, and preferably an alkoxy group having 1 to 4 carbon atoms. Specific examples thereof include a methoxy group, an ethoxy group, a 1-propoxy group, a 2-propoxy group, a 1-butoxy group, a 2-butoxy group, and a tert-butoxy group.

The halogeno group is, for example, a fluoro group, a chloro group, a bromo group, and an iodo group, and the fluoro group is preferred.

Each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group, and preferably represents a hydrogen atom. The alkyl group, cycloalkyl group, alkenyl group, aryl group and aralkyl group in $R^5$ to $R^{12}$ are the same as the groups described in detail in the description of $R^1$ to $R^4$ above. Each of $R^5$ to $R^{12}$ may be bonded to each other to form a ring.

The preferable form of the ruthenium complex ($1^A$) of the present invention includes a ruthenium complex represented by the following formula ($1^B$):

[Chem. 10]

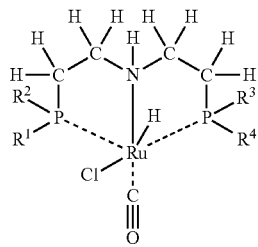

$1^B$

In the formula ($1^B$), the solid line represents a single bond, the triple line represents a triple bond, and the broken line represents a coordinate bond. C represents a carbon atom, H represents a hydrogen atom, N represents a nitrogen atom, O represents an oxygen atom, and P represents a phosphorus atom. Ru represents a divalent ruthenium ion, and Cl represents a chloride ion. Each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent. $R^1$ and $R^2$ may be bonded to each other to form a ring which may have a substituent. $R^3$ and $R^4$ may be bonded to each other to form a ring which may have a substituent.

Preferable specific examples of the ruthenium complex ($1^A$) of the present invention include (bis[2-(diphenyl-phosphino)ethyl]amine carbonylchlorohydridoruthenium(II) (Ru-MACHO) ($1^B$-1), {bis[2-(dicyclohexylphosphino)ethyl]amine}carbonylchlorohydridoruthenium(II) ($1^B$-2), {bis[2-(diisopropylphosphino)ethyl]amine}carbonylchlorohydridoruthenium(II) ($1^B$-3), {bis[2-(di-tert-butylphosphino)ethyl]amine}carbonylchlorohydridoruthenium(II) ($1^B$-4), and {bis[2-(di-1-adamantylphosphino)ethyl]amine}carbonylchlorohydridoruthenium(II) ($1^B$-5), of which structural formulae are shown below. Particularly preferable specific examples thereof include {bis[2-(diphenylphosphino)ethyl]amine}carbonyl-chlorohydridoruthenium(II) (Ru-MACHO) ($1^B$-1) and {bis[2-(dicyclohexylphosphino)ethyl]amine}carbonylchlorohydridoruthenium(II) ($1^B$-2).

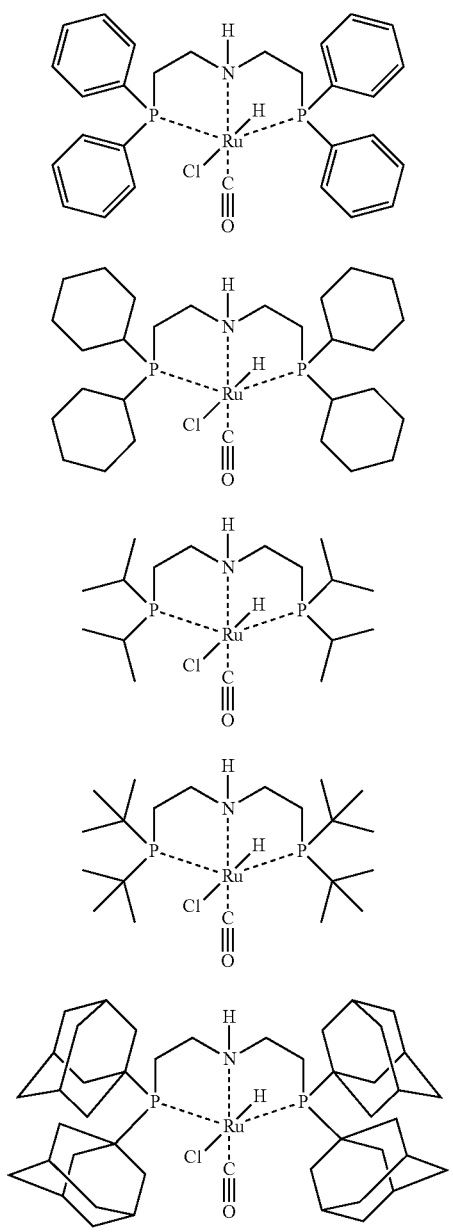

1<sup>B</sup>-1

1<sup>B</sup>-2

1<sup>B</sup>-3

1<sup>B</sup>-4

1<sup>B</sup>-5

The ruthenium dinuclear complex ($2^A$) serving as a ruthenium source of the ruthenium complex ($1^A$) of the present invention is described below. In the formula ($2^A$), the solid line represents a single bond, and the broken line represents a coordinate bond, Ru represents a divalent ruthenium ion, and X represents a halide ion. Specific examples of the halide ion include a fluoride ion, a chloride ion, a bromide ion, and an iodide ion, and preferable specific examples thereof include a chloride ion.

AH represents an aromatic hydrocarbon which may have a substituent. The aromatic hydrocarbon is, for example, an aryl group having 6 to 18 carbon atoms, and preferably an aryl group having 6 to 14 carbon atoms. Specific examples thereof include benzene, naphthalene, anthracene, and phenanthrene, and preferable specific examples thereof include benzene.

As the substituent that the aromatic hydrocarbon may have, preferable examples thereof include an alkyl group. The alkyl group may be linear or branched, and is, for example, an alkyl group having 1 to 10 carbon atoms, preferably an alkyl group having 1 to 8 carbon atoms, and more preferably an alkyl group having 1 to 6 carbon atoms. Specific examples thereof include a methyl group, an ethyl group, an n-propyl group, a 2-propyl group, an n-butyl group, a 2-butyl group, an isobutyl group, a tert-butyl group, an n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, and a 2,2-dimethylbutan-3-yl group, and preferable specific examples thereof include a methyl group and a 2-propyl group.

The preferable form of the ruthenium dinuclear complex ($2^A$) includes a ruthenium binuclear complex represented by the following formula ($2^B$):

[Chem. 12]

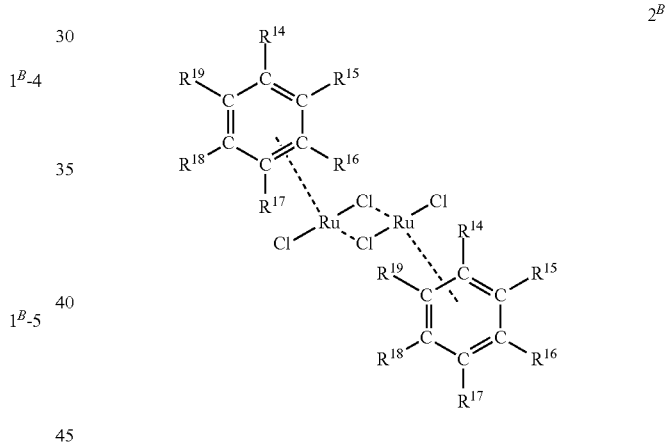

$2^B$

In the formula ($2^B$), the solid line represents a single bond, the double line represents a double bond, and the broken line represents a coordinate bond. C represents a carbon atom, Cl represents a chloride ion, and Ru represents a divalent ruthenium ion. Each of $R^{14}$, $R^{15}$, $R^{16}$, $R^{17}$, $R^{18}$ and $R^{19}$ independently represents a hydrogen atom or an alkyl group. The alkyl group in $R^{14}$ to $R^{19}$ is the same as the alkyl group described in detail as the substituent that the aromatic hydrocarbon above may have.

Preferable specific examples of the ruthenium dinuclear complex ($2^A$) include dichloro(p-cymene)ruthenium(II) dimer ($2^B$-1), dichloro(benzene)ruthenium(II) dimer ($2^B$-2), dichloro(mesitylene)ruthenium(II) dimer ($2^B$-3), dichloro(hexamethylbenzene)ruthenium(II) dimer ($2^B$-4), and diiodo(p-cymene)ruthenium(II) dimer ($2^A$-1), of which structural formulae are shown below. From a production aspect, particularly preferable specific examples thereof include dichloro(p-cymene)ruthenium(II) dimer ($2^B$-1).

[Chem. 13]

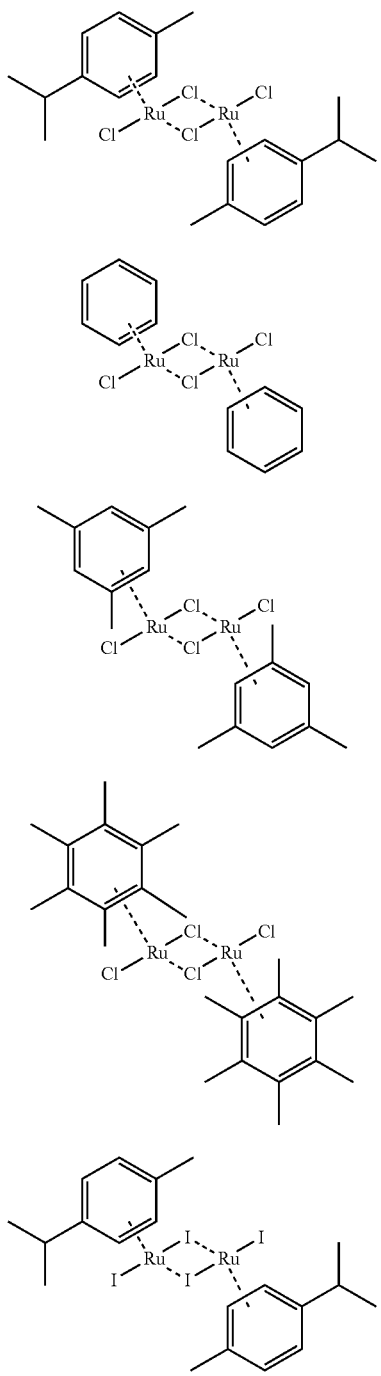

$2^B$-1

$2^B$-2

$2^B$-3

$2^B$-4

$2^A$-1

Next, the compound ($3^A$) serving as a ligand of the ruthenium complex ($1^A$) of the present invention is described. In the formula ($3^A$), the solid line represents a single bond. C represents a carbon atom, H represents a hydrogen atom, N represents a nitrogen atom, and P represents a phosphorus atom. $R^1$, $R^2$, $R^3$, $R^4$, $R^5$, $R^6$, $R^7$, $R^8$, $R^9$, $R^{10}$, $R^{11}$ and $R^{12}$ are exactly the same as those described in detail in the description of the ruthenium complex ($1^A$) of the present invention.

The preferable form of the compound ($3^A$) includes a compound represented by the following formula ($3^B$).

[Chem. 14]

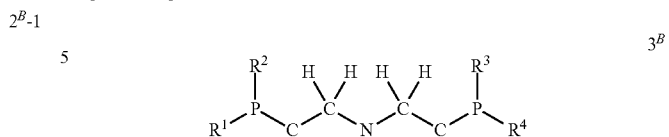

$3^B$

In the formula ($3^B$), the solid line represents a single bond. C represents a carbon atom, H represents a hydrogen atom, N represents a nitrogen atom, and P represents a phosphorus atom. Each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent. $R^1$ and $R^2$ may be bonded to each other to form a ring which may have a substituent. $R^3$ and $R^4$ may be bonded to each other to form a ring which may have a substituent.

Preferable specific examples of the compound ($3^A$) include bis[2-(diphenylphosphino)ethyl]amine ($3^B$-1), bis [2-(dicyclohexylphosphino)ethyl]amine ($3^B$-2), bis[2-(di-isopropylphosphino)ethyl]amine ($3^B$-3), bis[2-(di-tert-butylphosphino)ethyl]amine ($3^B$-4), and bis[2-(di-1-adamantylphosphino)ethyl]amine ($3^B$-5), of which structural formulae are shown below. In view of catalytic activity of the ruthenium complex ($1^A$) of the present invention, particularly preferable specific examples thereof include bis[(2-diphenylphosphino)ethyl]amine ($3^B$-1) and bis[(2-dicyclohexylphosphino)ethyl]amine ($3^B$-2).

[Chem. 15]

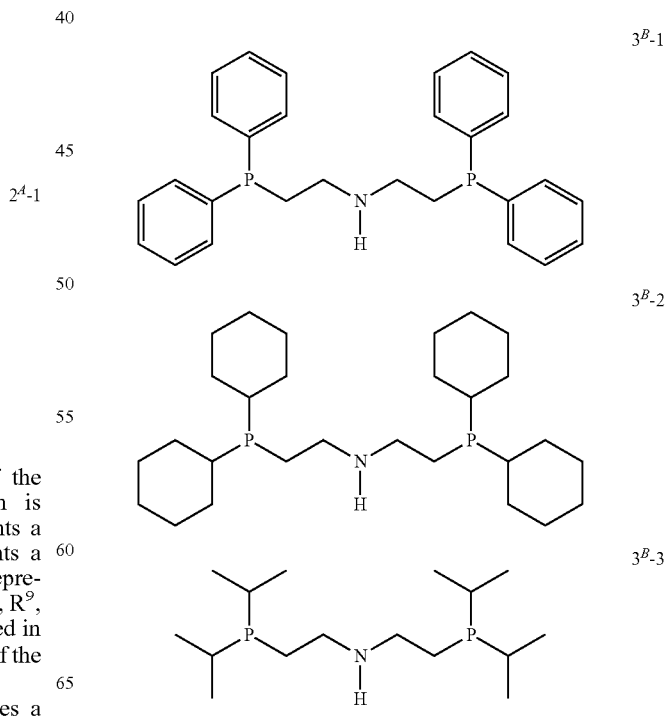

$3^B$-1

$3^B$-2

$3^B$-3

-continued

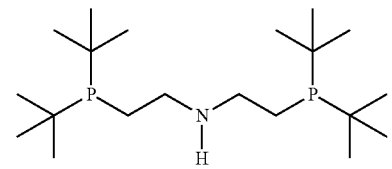

3^B-4

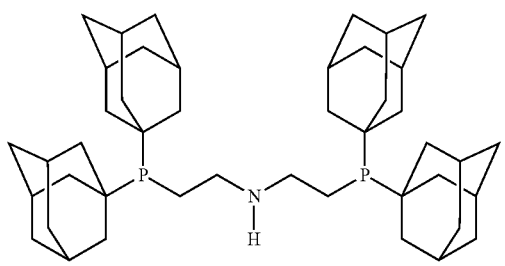

3^B-5

Some of the compounds (3^A) are difficult to weigh in usual way because of their unstability in air and/or their high-viscosity. Therefore, the compounds (3^A) may be transformed into the corresponding salt by treating with a Bronsted acid for improving their stability or crystallinity. The Bronsted acid is not particularly limited as long as it is an acid capable of giving the salt of the compound (3^A), but examples thereof include perchloric acid, nitric acid, tetrafluoroboric acid, hexafluorophosphoric acid, hexafluoroantimonic acid, hydrohalic acid, and sulfonic acid, and hydrohalic acid is preferred.

Specific examples of the hydrohalic acid include hydrofluoric acid, hydrochloric acid, hydrobromic acid, and hydroiodic acid, and preferable specific examples thereof include hydrochloric acid.

Specific examples of the sulfonic acid include methanesulfonic acid, trifluoromethanesulfonic acid, p-toluenesulfonic acid, and 10-camphorsulfonic acid.

Particularly preferable specific example of the salt of the compound (3^A) includes bis[2-(diphenylphosphino)ethyl]amine hydrochloride (3^B-1_HCl), of which structural formula is shown below.

[Chem. 16]

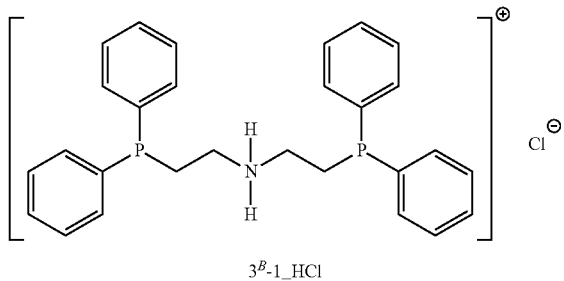

3^B-1_HCl

In the case of using a salt of the compound (3^A) for the production of the ruthenium complex (1^A), the compound (3^A) may be liberated by treating the salt of the compound (3^A) with the later-described base outside of the reaction system and then allowed to react with the ruthenium dinuclear complex (2^A), or the compound (3^A) may be allowed to react with the ruthenium dinuclear complex (2^A) while liberating the compound (3^A) by treating the salt of the compound (3^A) with the later-described base in the reaction system.

Next, the ruthenium dinuclear complex (4^A) serving as a synthetic intermediate of the ruthenium complex (1^A) of the present invention is described. In the formula (4^A), the solid line represents a single bond and the broken line represents a coordinate bond. C represents a carbon atom, H represents a hydrogen atom, N represents a nitrogen atom, P represents a phosphorus atom, Ru represents a divalent ruthenium ion, and X represents a halide ion.

Specific examples of the halide ion include a fluoride ion, a chloride ion, a bromide ion, and an iodide ion, and preferable specific examples thereof include a chloride ion. $R^1$, $R^2$, $R^3$, $R^4$, $R^5$, $R^6$, $R^7$, $R^8$, $R^9$, $R^{10}$, $R^{11}$ and $R^{12}$ are exactly the same as those described in detail in the description of the ruthenium complex (1^A) of the present invention.

Examples of the preferable form of the ruthenium dinuclear complex (4^A) include a ruthenium dinuclear complex represented by the following formula (4^B).

[Chem. 17]

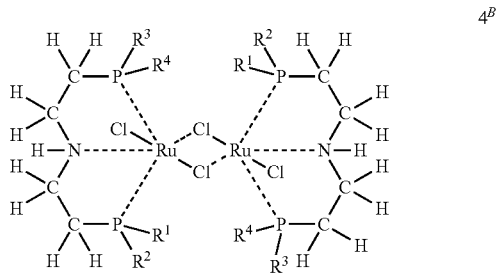

4^B

In the formula (4^B), the solid line represents a single bond and the broken line represents a coordinate bond. C represents a carbon atom, H represents a hydrogen atom, N represents a nitrogen atom, and P represents a phosphorus atom. Ru represents a divalent ruthenium ion, and Cl represents a chloride ion. Each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent. $R^1$ and $R^2$ may be bonded to each other to form a ring which may have a substituent. $R^3$ and $R^4$ may be bonded to each other to form a ring which may have a substituent.

Particularly preferable specific examples of the ruthenium dinuclear complex (4^A) include dichloro{bis[2-(diphenylphosphino)ethyl]amine}ruthenium(II) dimer (4^B-1) and dichloro{bis[2-(dicyclohexylphosphino)ethyl]amine}ruthenium(II) dimer (4^B-2), of which structural formulae are shown below.

[Chem. 18]

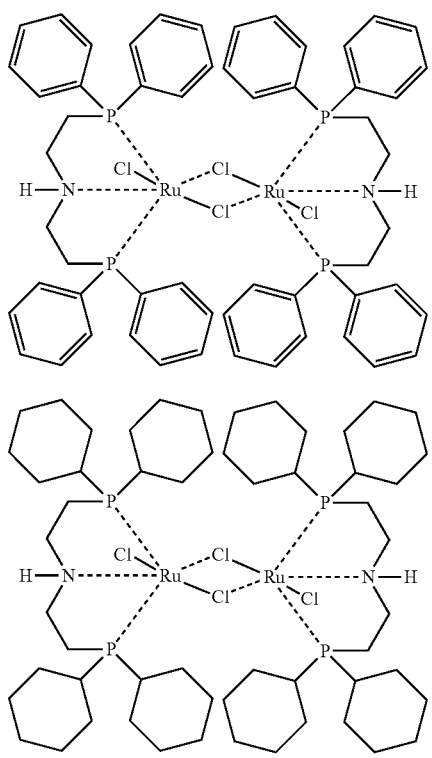

This ruthenium dinuclear complex ($4^A$) can be easily produced by reacting the ruthenium dinuclear complex ($2^A$) with the compound ($3^A$) in a solvent. The thus-obtained ruthenium dinuclear complex ($4^A$) may be subjected to isolation and purification or may not be subjected to isolation and purification, and converted to the ruthenium complex ($1^A$) of the present invention by treating with a primary alcohol and a base.

Next, the primary alcohol in the production method of the present invention is described in detail. First of all, the primary alcohol in the production method of the present invention represents a compound having at least one hydroxymethyl group, represented by the formula: R—$CH_2$—OH (wherein the solid line represents a single bond, $CH_2$ represents a methylene group, OH represents a hydroxyl group, and R represents a hydrogen atom or a substituent).

The ruthenium complex ($1^A$) of the present invention can be easily produced by reacting the ruthenium dinuclear complex ($2^A$) with the compound ($3^A$) in the presence of a primary alcohol and a base. In addition, the ruthenium complex ($1^A$) of the present invention can also be easily produced by treating the ruthenium dinuclear complex ($4^A$) with a primary alcohol and a base.

Both the primary alcohol and the base are essential compounds for introducing a hydride ligand (H) and a carbonyl ligand (C—O) into the divalent ruthenium ion (Ru) in the ruthenium complex ($1^A$) of the present invention. In order to describe the essentials of the primary alcohol and the base in the production method of the present invention, an outline of a putative reaction mechanism for introducing the hydride ligand and the carbonyl ligand into the divalent ruthenium ion is shown in the following Eq. 4.

That is, a ruthenium alkoxide intermediate (Int-1) is thought to be produced firstly by reacting the ruthenium dinuclear complex ($2^A$) with the compound ($3^A$) in the presence of a primary alcohol and a base (Step 1). Int-1 is also thought to be produced as an intermediate by treating the ruthenium dinuclear complex ($4^A$) with a primary alcohol and a base. It is presumed that a ruthenium hydride intermediate (Int-2) is then produced by β-hydride elimination from Int-1 (Step 2) and subsequently, a decarbonylation reaction from Int-2 (Step 3) occurs to produce the ruthenium complex ($1^A$) of the present invention. The present invention is not limited by this outline.

[Chem. 19]

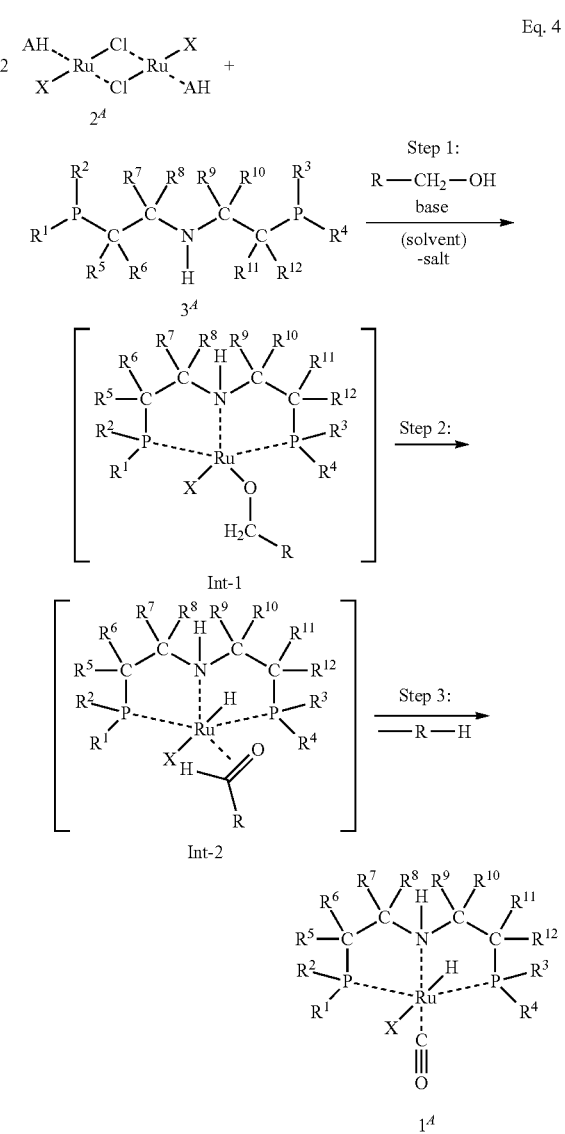

As seen from the outline of the putative reaction mechanism (Eq. 4), any primary alcohol can be used for the introduction of a hydride ligand and a carbonyl ligand into the divalent ruthenium ion. However, in this reaction, a compound represented by the formula: R—H (wherein the solid line represents a single bond, H represents a hydrogen atom, and R represents a hydrogen atom or a substituent) is produced as a by-product from the primary alcohol, and the by-product may adversely affect the yield and purity of the ruthenium complex ($1^{-4}$) of the present invention if the by-product has high coordination ability to the divalent ruthenium ion or low stability to base. From such a viewpoint, examples of the preferable form of the primary alcohol include an alcohol represented by the formula (5) [hereinafter, referred to as alcohol (5)].

In the formula (5), the solid line represents a single bond. C represents a carbon atom, H represents a hydrogen atom, and O represents an oxygen atom. $R^{13}$ represents a hydrogen atom or a group selected from the group consisting of an alkyl group which may have a substituent, a cycloalkyl group which may have a substituent, an alkenyl group which may have a substituent, an aryl group which may have a substituent, an oxygen-containing aliphatic heterocyclic group which may have a substituent, and an oxygen-containing heteroaryl group which may have a substituent, and preferably represents a hydrogen atom or an alkyl group which may have a substituent.

The alkyl group may be linear or branched, and is, for example, an alkyl group having 1 to 19 carbon atoms, preferably an alkyl group having 1 to 14 carbon atoms, and more preferably an alkyl group having 1 to 9 carbon atoms. Specific examples thereof include a methyl group, an ethyl group, an n-propyl group, a 2-propyl group, an n-butyl group, a 2-butyl group, an isobutyl group, a tert-butyl group, an n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, an n-heptyl group, an n-octyl group, and an n-nonyl group, and preferable specific examples thereof include an n-propyl group.

The cycloalkyl group may be monocyclic or polycyclic, and is, for example, a cyclohexyl group having 3 to 19 carbon atoms, preferably a cycloalkyl group having 3 to 14 carbon atoms, and more preferably a cycloalkyl group having 3 to 6 carbon atoms. Specific examples thereof include a cyclopropyl group, a cyclobutyl group, a cyclopentyl group, and a cyclohexyl group.

The alkenyl group may be linear, branched or cyclic, and is, for example, an alkenyl group having 2 to 14 carbon atoms, preferably an alkenyl group having 2 to 8 carbon atoms, and more preferably an alkenyl group having 2 to 6 carbon atoms. Specific examples thereof include a vinyl group, a 1-propenyl group, a 2-propenyl group, an allyl group, and a 1-cyclohexenyl group.

The aryl group is, for example, an aryl group having 6 to 18 carbon atoms, preferably an aryl group having 6 to 14 carbon atoms, and more preferably an aryl group having 6 to 10 carbon atoms. Specific examples thereof include a phenyl group, a 1-naphthyl group, and a 2-naphthyl group.

The oxygen-containing aliphatic heterocyclic group is, for example, a 5- or 6-membered aliphatic heterocyclic group containing 1 or 2 oxygen atoms as a heteroatom. Specific examples thereof include a tetrahydrofuran-2-yl group, a tetrahydrofuran-3-yl group, a tetrahydropyran-2-yl group, a tetrahydropyran-3-yl group, a tetrahydropyran-4-yl group, a 1,3-dioxan-2-yl group, and a 1,4-dioxan-2-yl group.

The oxygen-containing heteroaryl group is, for example, heteroaryl groups derived from furan and benzofuran. Specific examples thereof include a 2-furyl group, a 3-furyl group, a 2-benzofuryl group, and a 3-benzofuryl group.

As the substituent that the alkyl group and cycloalkyl group in $R^{13}$ may have, examples thereof include an alkenyl group, an aryl group, an oxygen-containing aliphatic heterocyclic group, an oxygen-containing heteroaryl group, a hydroxyl group, an alkoxy group, and an aryloxy group, and an alkoxy group is preferred. Of these groups, the alkenyl group, aryl group, oxygen-containing aliphatic heterocyclic group and oxygen-containing heteroaryl group are the same as the groups described in detail in the description of $R^{13}$ above.

The alkoxy group may be linear or branched, and is, for example, an alkoxy group having 1 to 10 carbon atoms, and preferably an alkoxy group having 1 to 4 carbon atoms. Specific examples thereof include a methoxy group, an ethoxy group, a 1-propoxy group, a 2-propoxy group, a 1-butoxy group, a 2-butoxy group, and a tert-butoxy group, and preferable specific examples thereof include a methoxy group.

The aryloxy group is, for example, an aryloxy group having 6 to 18 carbon atoms, preferably an aryloxy group having 6 to 14 carbon atoms, and more preferably an aryloxy group having 6 to 10 carbon atoms. Specific examples thereof include a phenoxy group, a 1-naphthyloxy group, and a 2-naphthyloxy group.

As the substituent that the alkenyl group, aryl group and oxygen-containing heteroaryl group in $R^{13}$ may have, examples thereof include an alkyl group, a cycloalkyl group, an alkenyl group, an aryl group, an oxygen-containing aliphatic heterocyclic group, an oxygen-containing heteroaryl group, an alkoxy group, and an aryloxy group. Of these groups, the alkyl group, cycloalkyl group, alkenyl group, aryl group, oxygen-containing aliphatic heterocyclic group and oxygen-containing heteroaryl group are the same as the groups described in detail in the description of $R^3$ above. In addition, the alkoxy group and aryloxy group are the same as the groups described in detail in the description of the substituent that the alkyl group and cycloalkyl group in $R^{13}$ above may have.

As the substituent that the oxygen-containing aliphatic heterocyclic group in $R^{13}$ may have, examples thereof include an alkyl group, a cycloalkyl group, an alkenyl group, an aryl group, an oxygen-containing aliphatic heterocyclic group, an oxygen-containing heteroaryl group, a hydroxyl group, an alkoxy group, and an aryloxy group. Of these groups, the alkyl group, cycloalkyl group, alkenyl group, aryl group, oxygen-containing aliphatic heterocyclic group and oxygen-containing heteroaryl group are the same as the groups described in detail in the description of $R^{13}$ above. In addition, the alkoxy group and aryloxy group are the same as the groups described in detail in the description of the substituent that the alkyl group and cycloalkyl group in $R^{13}$ above may have.

Particularly preferable specific examples of the alcohol (5) include 1-butanol and 3-methoxy-1-butanol.

Next, the base used together with the primary alcohol above in the production method of the present invention is described in detail. The base is not particularly limited as long as it is a base capable of giving the ruthenium alkoxide intermediate (Int-1) in the outline of the putative reaction mechanism (Eq. 4) in the co-presence of the primary alcohol, and examples of the base include an alkali metal hydroxide, an alkaline earth metal hydroxide, an alkali metal carbonate, an alkali metal phosphate, an alkali metal alkoxide, and amidines, and preferable examples thereof include an alkali metal hydroxide, an alkali metal alkoxide, and amidines.

Specific examples of the alkali metal hydroxide include lithium hydroxide, sodium hydroxide, and potassium hydroxide, and preferable specific examples thereof include sodium hydroxide.

Specific examples of the alkaline earth metal hydroxide include calcium hydroxide, strontium hydroxide, and barium hydroxide.

Specific examples of the alkali metal carbonate include lithium carbonate, sodium carbonate, and potassium carbonate.

Specific examples of the alkali metal phosphate include trisodium phosphate and tripotassium phosphate.

Examples of the alkali metal alkoxide include an alkali metal primary alkoxide, an alkali metal secondary alkoxide, and an alkali metal tertiary alkoxide. Specific examples thereof include lithium methoxide, lithium ethoxide, lithium 2-propoxide, lithium tert-butoxide, lithium tert-pentoxide, sodium methoxide, sodium ethoxide, sodium 2-propoxide, sodium tert-butoxide, sodium tert-pentoxide, potassium methoxide, potassium ethoxide, potassium tert-butoxide, and potassium tert-pentoxide, and preferable specific examples thereof include sodium methoxide, sodium ethoxide, and sodium tert-butoxide.

Specific examples of the amidines include 1,5-diazabicyclo[4.3.0]-5-nonene and 1,8-diazabicyclo[5.4.0]-7-undecene, and preferable specific examples thereof include 1,8-diazabicyclo[5.4.0]-7-undecene.

In addition, a compound capable of reacting with the primary alcohol above to give a corresponding alkali metal primary alkoxide can also be used as a base equivalent. Examples of the base equivalent include, for example, an alkali metal, an alkali metal oxide, an alkali metal hydride, an organolithium compound, and an alkali metal amide, and preferable examples thereof include an alkali metal hydride.

Specific examples of the alkali metal include lithium, sodium, and potassium.

Specific examples of the alkali metal oxide include lithium oxide, sodium oxide, and potassium oxide.

Specific examples of the alkali metal hydride include lithium hydride, sodium hydride, and potassium hydride, and preferable specific examples thereof include sodium hydride.

Specific examples of the organolithium compound include methyllithium, ethyllithium, 2-propyllithium, n-butyllithium, isobutyllithium, sec-butyllithium, and tert-butyllithium.

Specific examples of the alkali metal amide include lithium amide, lithium diisopropylamide, lithium bis(trimethylsilyl)amide, sodium amide, sodium bis(trimethylsilyl)amide, and potassium bis(trimethylsilyl)amide.

The used amount of the base or base equivalent is not particularly limited but is appropriately selected in a range of usually from 1 to 15 equivalents, preferably from 1.2 to 10 equivalents, more preferably from 1.5 to 5 equivalents, relative to the ruthenium dinuclear complex ($2^A$) and the ruthenium dinuclear complex ($4^A$). The base or base equivalent may be used for liberating the compound ($3^A$) from the above-described salt of the compound ($3^A$).

The production method of the present invention is preferably conducted in the presence of a solvent. The solvent is not particularly limited as long as it is a solvent not inhibiting the reaction, but examples of the solvent include an aliphatic hydrocarbon, an aromatic hydrocarbon, a secondary alcohol, a tertiary alcohol, ethers, amides, sulfoxides, and water.

Specific examples of the aliphatic hydrocarbon include n-pentane, n-hexane, n-heptane, n-octane, n-decane, cyclohexane, and decalin.

Specific examples of the aromatic hydrocarbon include benzene, toluene, xylene, mesitylene, hexamethylbenzene, p-cymene, and 1,4-diisopropylbenzene.

Specific examples of the secondary alcohol include 2-propanol and cyclohexanol.

Specific examples of the tertiary alcohols include tert-butanol and 2-methyl-2-butanol.

Specific examples of the ethers include diethyl ether, diisopropyl ether, tert-butyl methyl ether, cyclopentyl methyl ether, dimethoxyethane, ethylene glycol diethyl ether, tetrahydrofuran, and 1,4-dioxane.

Specific examples of the amides include N,N-dimethylformamide and N,N-dimethylacetamide.

Specific examples of the sulfoxides include dimethylsulfoxide.

Each of these solvents may be used alone, or two or more thereof may be used in appropriate combination.

In the production method of the present invention, the primary alcohol above is preferably used not only as a reactant but also as a solvent. Examples of the preferable form of the primary alcohol used as a solvent include, among the above-described alcohols (5), an alcohol that is liquid at normal temperature and normal pressure. Preferable specific examples thereof include 1-butanol and 3-methoxy-1-butanol.

The production method of the present invention is preferably conducted in an inert gas atmosphere. Specific examples of the inert gas include argon gas and nitrogen gas, and preferable specific examples thereof include nitrogen gas.

The reaction temperature is appropriately selected in a range of usually from 0 to 300° C., preferably from 25 to 250° C., and more preferably from 50 to 200° C. The production method of the present invention is preferably conducted at atmospheric pressure but may be conducted under a condition of pressure or a condition of reduced pressure so as to adjust the reaction temperature. The reaction time is appropriately selected in a range of usually from 1 minute to 24 hours, preferably from 5 minutes to 12 hours, more preferably from 10 minutes to 6 hours.

As shown in the following Eq. 5, a ruthenium complex represented by the formula ($1^B$) can be produced in the same manner as the ruthenium complex ($1^A$) of the present invention, by reacting a ruthenium dinuclear complex represented by the formula ($2^B$) with a compound represented by the formula ($3^B$) in the presence of a primary alcohol and a base according to the production method above.

In addition, a ruthenium complex represented by the formula ($1^B$) can be produced in the same manner as the ruthenium complex ($1^A$) of the present invention, by treating a ruthenium dinuclear complex represented by the formula ($4^B$) with a primary alcohol and a base according to the production method above.

[Chem. 20]

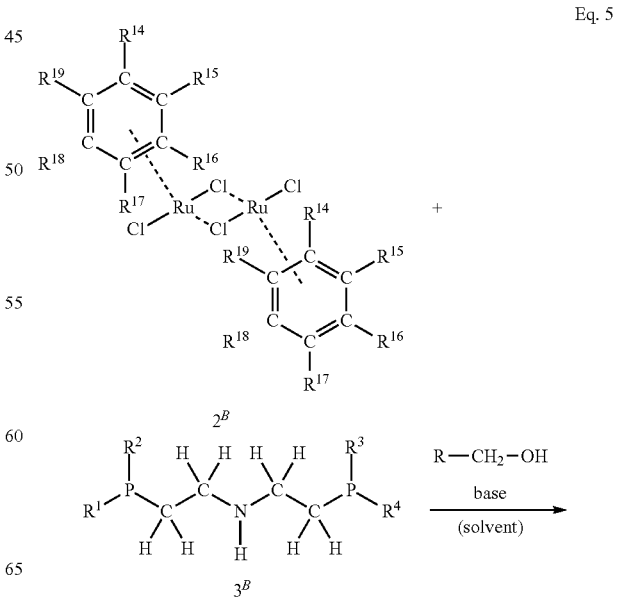

Eq. 5

-continued

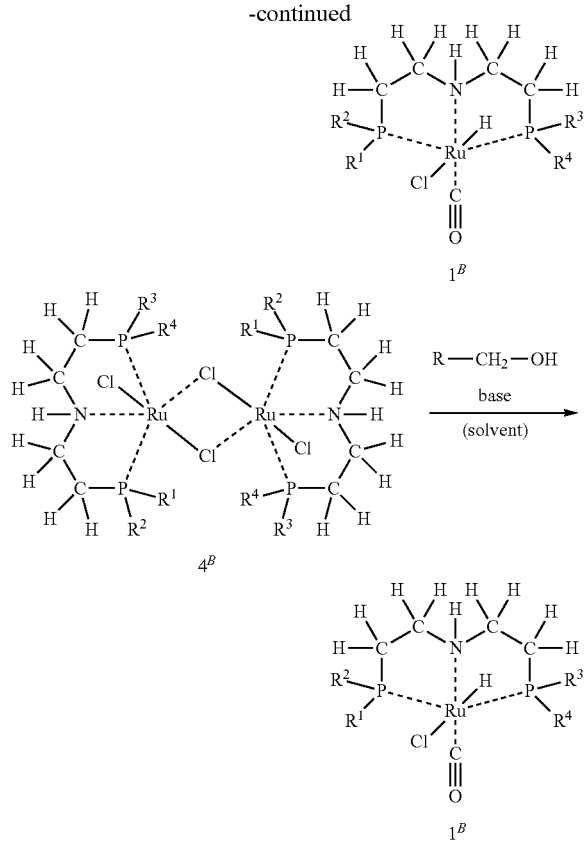

The ruthenium complex ($1^A$) of the present invention obtained in this way can be, if desired, subjected to post-treatment, isolation and purification. Examples of the method for post-treatment include concentration, solvent replacement, water washing, extraction, filtration and crystallization. These methods may be performed independently or in combination. Examples of the method for isolation and purification include decolorization with an adsorbent, column chromatography, and recrystallization. These methods may be performed independently or in combination.

The ruthenium complex ($1^A$) of the present invention obtained by the production method of the present invention has excellent purity and therefore can be suitably used for various organic chemical catalytic conversion reactions including a hydrogenation reaction.

EXAMPLES

The production method of the present invention is described in detail below by referring to Examples, but the present invention is not limited by these Examples. The apparatuses and conditions used for the measurements of physical properties in Examples are as follows.

1) Proton nuclear magnetic resonance spectroscopy ($^1$H NMR): Model 400MR DD2 spectrometer (resonance frequency: 400 MHz, manufactured by Agilent Technologies, Inc.), deuterated solvent: deuterated methylene chloride ($CD_2Cl_2$), internal standard substance: residual dichloromethane (5.32 ppm, triplet peak);

2) Phosphorus 31 nuclear magnetic resonance spectroscopy ($^{31}$P NMR): Model 400MR DD2 spectrometer (resonance frequency: 161 MHz, manufactured by Agilent Technologies, Inc.), external standard substance: phosphoric acid (0 ppm, singlet peak) in heavy water Examples 1-1 to 1-4 are related to the method for producing the ruthenium complex ($1^A$) of the present invention by reacting the ruthenium dinuclear complex ($2^A$) with the compound ($3^A$) in the presence of a primary alcohol and a base. Examples 2-1 to 2-6 are related to the method for producing the ruthenium complex ($1^A$) of the present invention by treating, and the ruthenium dinuclear complex ($4^A$) with a primary alcohol and a base. Examples 3-1 to 3-3 and Example 4 are related to the method for producing the ruthenium complex ($1^A$) of the present invention by treating the crude product of the ruthenium dinuclear complex ($4^A$) with a primary alcohol and a base. In each of Examples, substrates and a solvent were charged under nitrogen flow, the reaction was conducted under nitrogen atmosphere, and post-treatment, isolation and purification were conducted in air.

(Example 1-1) Production of {bis[2-(diphenylphosphino)-ethyl]amine}carbonylchlorohydridoruthenium(II) (Ru-MACHO) ($1^B$-1) by Reacting dichloro(p-cymene)ruthenium(II) dimer ($2^B$-1) with bis[2-(diphenylphosphino)ethyl]amine ($3^B$-1) in the Presence of a Primary Alcohol and a Base The reaction formula is shown in the following Eq. 6.

[Chem. 21]

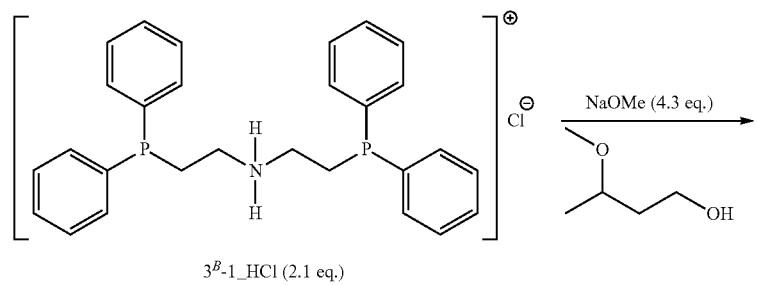

Eq. 6

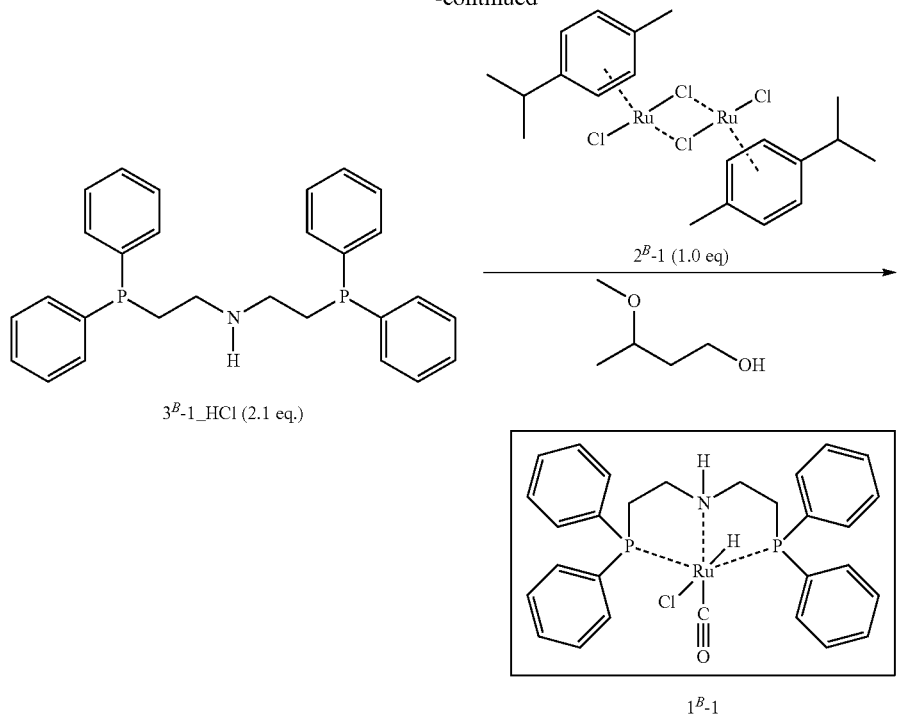

(Setup and Reaction)

A 100 mL four-necked round-bottomed flask equipped with a magnetic stirring bar, condenser, Claisen distillation apparatus, thermometer, and a three-way stopcock was evacuated and filled with nitrogen gas. Then, 3-methoxy-1-butanol (boiling point: 157° C., 60 mL), sodium methoxide (NaOMe) (purity: 99.1 mass %, 1.53 g, 28.08 mmol, 4.3 equivalents), and bis[2-(diphenylphosphino)ethyl]amine hydrochloride ($3^B$-1_HCl) (6.56 g, 13.71 mmol, 2.1 equivalents) were charged into the flask successively.

The obtained white suspension was stirred at room temperature for 30 minutes, and a neutralization reaction thereby proceeded while precipitating sodium chloride, and as a result, a mixture of bis[2-(diphenylphosphino)ethyl]amine ($3^B$-1) (2.1 equivalents) and NaOMe (2.2 equivalents) was obtained as a white suspension.

Dichloro(p-cymene)ruthenium(II) dimer ($2^B$-1) (4.0 g, 6.53 mmol, 1.0 equivalent) was added to the suspension above, and the resulting orange suspension was stirred under reflux for 1 hour while distilling off low-boiling-point compounds by means of the Claisen distillation apparatus.

(Post-Treatment, Isolation, and Purification)

The light brown suspension obtained after the reaction was cooled to 5° C. by using an ice-water bath and filtered by suction, and the obtained crystal was washed with methanol, water and methanol successively and dried by heating under reduced pressure to give 6.07 g of the title compound ($1^B$-1) as a light yellow powder. Isolated yield: 76.6%.

$^1$H NMR (400 MHz, CD$_2$Cl$_2$): δ=7.86-7.75 (m, 8H), 7.45-7.38 (m, 12H), 3.89 (br t, 1H), 3.53-3.36 (m, 2H), 3.05-2.95 (m, 2H), 2.62-2.44 (m, 4H), −15.2 (t, J=19.6 Hz, 1H).

$^{31}$P NMR (161 MHz, CD$_2$Cl$_2$): δ=52.8 (d, J=6.0 Hz, 2P).

A coordination isomer [δ=55.4 (d, J=6.1 Hz, 2P)] produced as a by-product in the conventional production method was not observed at all.

(Example 1-2) Production of Ru-MACHO ($1^B$-1) by Using Sodium Ethoxide as a Base 5.15 g of the title compound ($1^B$-1) was obtained as a light yellow powder by carrying out the same operation as in Example 1-1 except that sodium ethoxide (NaOEt) (purity: 98.0 mass %, 1.95 g, 28.08 mmol, 4.3 equivalents) was used in place of NaOMe. Isolated yield: 65.0%.

(Example 1-3) Production of Ru-MACHO ($1^B$-1) by Using Sodium Tert-Butoxide as a Base 5.94 g of the title compound ($1^B$-1) was obtained as a light yellow powder by carrying out the same operation as in Example 1-1 except that sodium tert-butoxide (NaO$^t$Bu) (purity: 99.1 mass %, 2.72 g, 28.08 mmol, 4.3 equivalents) was used in place of NaOMe. Isolated yield: 74.9%.

(Example 1-4) Production of Ru-MACHO ($1^B$-1) by Using 1-Butanol as a Primary Alcohol 5.94 g of the title compound ($1^B$-1) was obtained as a light yellow powder by carrying out the same operation as in Example 1-1 except that 1-butanol (boiling point: 117° C., 60 mL) was used in place of 3-methoxy-1-butanol. Isolated yield: 74.9%.

The results of Examples 1-1 to 1-4 are summarized in Table 1 below.

TABLE 1

| Example | Primary Alcohol | Base | Isolated Yield |
| --- | --- | --- | --- |
| 1-1 | 3-methoxy-1-butanol | NaOMe | 76.6% |
| 1-2 | 3-methoxy-1-butanol | NaOEt | 65.0% |
| 1-3 | 3-methoxy-1-butanol | NaO$^t$Bu | 74.9% |
| 1-4 | 1-butanol | NaOMe | 74.9% |

As seen from Table 1, Ru-MACHO ($1^B$-1) as a kind of ruthenium complex ($1^A$) of the present invention was obtained as a single isomer in good yield by reacting $2^B$-1 as a kind of ruthenium dinuclear complex ($2^A$) with $3^B$-1 as a kind of compound ($3^A$) in the presence of a primary alcohol and a base. In addition, all of by-products of this reaction could be easily removed by filtration of the reaction mixture and washing with methanol and water.

(Example 2-1) Production of (bis[2-(diphenylphosphino)-ethyl]amine) carbonylchlorohydridoruthenium(II) (Ru-MACHO) ($1^B$-1) by Treating dichloro{bis[2-(diphenylphosphino)ethyl]amine}ruthenium(II) dimer ($4^B$-1) with a Primary Alcohol and a Base The reaction formula is shown in the following Eq. 7.

First Step: Production of dichloro({bis[2-(diphenylphosphino)ethyl]amine}ruthenium(II) dimer ($4^B$-1)

(Setup and Reaction)

A 200 mL four-necked round-bottomed flask equipped with a magnetic stirring bar, condenser, thermometer, and a three-way stopcock was evacuated and filled with nitrogen gas. Then, 3-methoxy-1-butanol (boiling point: 157° C., 100 mL), NaOMe (purity: 99.1 mass %, 2.4 g, 43.6 mmol, 2.15 equivalents), and bis[2-(diphenylphosphino)ethyl]amine hydrochloride ($3^B$-1_HCl) (21.3 g, 44.6 mmol, 2.2 equivalents) were charged into the flask successively.

The obtained white suspension was stirred at room temperature for 30 minutes, and a neutralization reaction thereby proceeded while precipitating sodium chloride, and as a result, a 3-methoxy-1-butanol solution of bis[2-(diphenylphosphino)ethyl]amine ($3^B$-1) (2.15 equivalents) was obtained as a white suspension.

[Chem. 22]

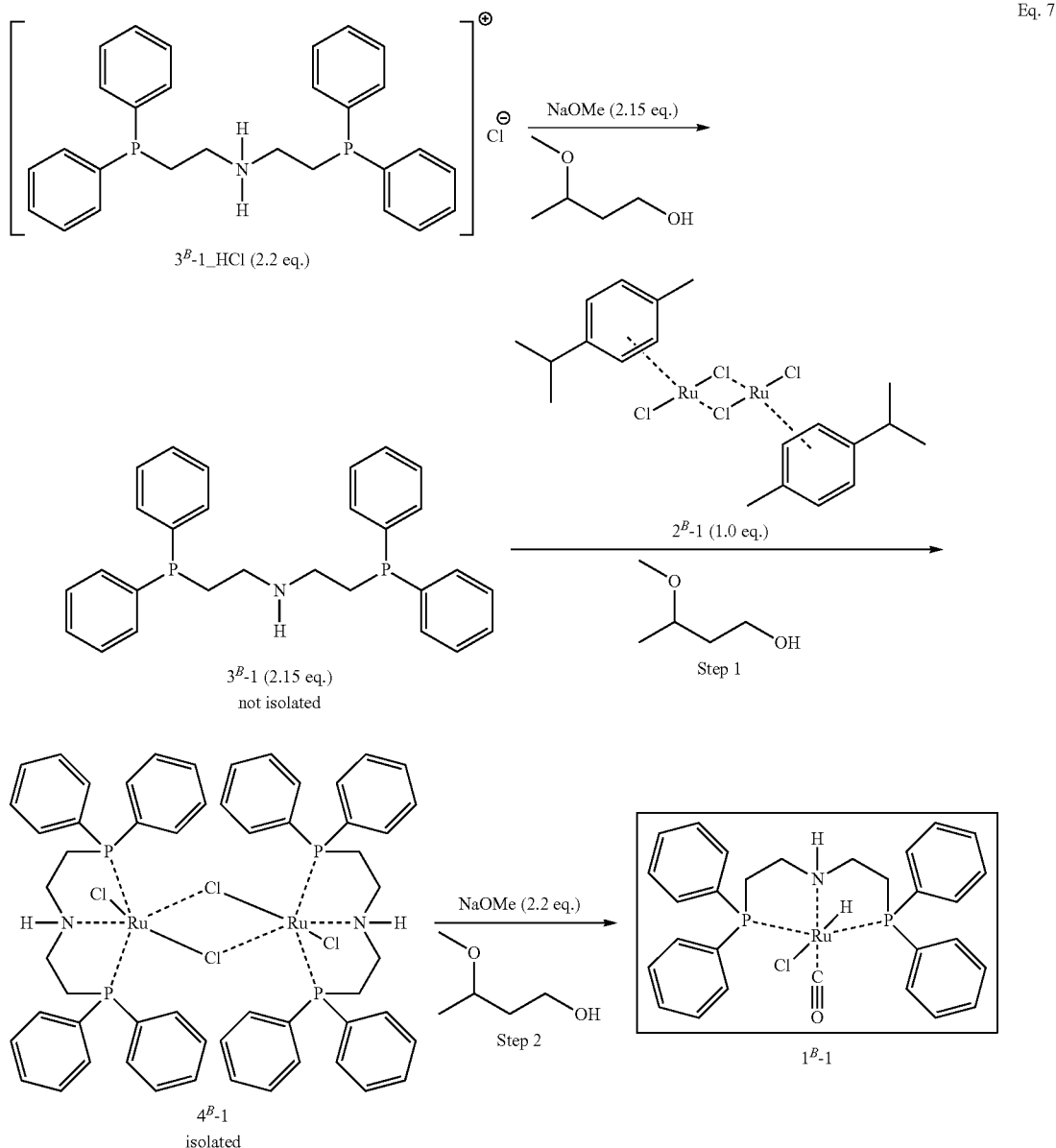

Eq. 7

Dichloro(p-cymene)ruthenium(II) dimer ($2^B$-1) (4.0 g, 6.53 mmol, 1.0 equivalent) was added to the suspension above, and the resulting red suspension was stirred under reflux for 1 hour.

(Post-Treatment, Isolation, and Purification)

The orange suspension obtained after the reaction was cooled to 5° C. by using an ice-water bath and filtered by suction, and the obtained crystal was washed with methanol, water and methanol successively and dried by heating under reduced pressure to give 24.1 g of the title compound ($4^B$-1) as an orange powder. Isolated yield: 96.8%.

$^1$H NMR (400 MHz, $CD_2Cl_2$): 7.82-7.73 (m, 8H), 7.12-7.02 (m, 20H), 6.87 (t, J=7.2 Hz, 4H), 6.78-6.69 (m, 10H), 3.48-3.32 (m, 4H), 2.98-2.81 (m, 4H), 2.79-2.66 (m, 4H), 2.22-2.08 (m, 4H).

$^{31}$P NMR (161 MHz, $CD_2Cl_2$): δ=64.2 (s, 4P).

Second Step: Production of {bis[2-(diphenylphosphino)-ethyl]amine}carbonylchlorohydridoruthenium(II) (Ru-MACHO) ($1^B$-1)

(Setup and Reaction)

A 50 mL four-necked round-bottomed flask equipped with a magnetic stirring bar, condenser, Claisen distillation apparatus, thermometer, and a three-way stopcock was evacuated and filled with nitrogen gas. Then, 3-methoxy-1-butanol (boiling point: 157° C., 30 mL), NaOMe (purity: 99.1 mass %, 391 mg, 7.17 mmol, 2.2 equivalents), and dichloro{bis [2-(diphenylphosphino)ethyl]amine}ruthenium(II) dimer ($4^B$-1) (4.0 g, 3.26 mmol, 1.0 equivalent) obtained in the first step were charged into the flask successively. The resulting orange suspension was stirred under reflux for 1 hour while distilling off low-boiling-point compounds by means of the Claisen distillation apparatus.

(Post-Treatment, Isolation, and Purification)

The light brown suspension obtained after the reaction was cooled to 5° C. by using an ice-water bath and filtered by suction, and the obtained crystal was washed with methanol, water and methanol successively and dried by heating under reduced pressure to give 3.35 g of the title compound ($1^B$-1) as a light yellow powder. Isolated yield: 84.6%. The NMR measurement results of this compound were consistent with those obtained in Example 1-1.

(Example 2-2) Production of Ru-MACHO ($1^B$-1) by Using 1,8-diazabicyclo[5.4.0]-7-undecene as a Base 3.46 g of the title compound ($1^B$-1) was obtained as a light yellow powder by carrying out the same operation as in Example 2-1 except that 1,8-diazabicyclo[5.4.0]-7-undecene (DBU) (1.07 mL, 7.17 mmol, 2.2 equivalents) was used in place of NaOMe. Isolated yield: 87.4%.

(Example 2-3) Production of Ru-MACHO ($1^B$-1) by Using Sodium Hydroxide as a Base 2.60 g of the title compound ($1^B$-1) was obtained as a light yellow powder by carrying out the same operation as in Example 2-1 except that sodium hydroxide (NaOH) (287 mg, 7.17 mmol, 2.2 equivalents) was used in place of NaOMe. Isolated yield: 65.7%.

(Example 2-4) Production of Ru-MACHO (1-1) by Using Sodium Ethoxide as a Base 3.39 g of the title compound ($1^B$-1) was obtained as a light yellow powder by carrying out the same operation as in Example 2-1 except that NaOEt (purity: 98.0 mass %, 498 mg, 7.17 mmol, 2.2 equivalents) was used in place of NaOMe. Isolated yield: 85.6%.

(Example 2-5) Production of Ru-MACHO ($1^B$-1) by Using Sodium Tert-Butoxide as a Base 3.24 g of the title compound ($1^B$-1) was obtained as a light yellow powder by carrying out the same operation as in Example 2-1 except that NaO$^t$Bu (purity: 99.1 mass %, 695 mg, 7.17 mmol, 2.2 equivalents) was used in place of NaOMe. Isolated yield: 81.9%.

(Example 2-6) Production of Ru-MACHO ($1^B$-1) by Using Sodium Hydride as a Base Equivalent 3.40 g of the title compound ($1^B$-1) was obtained as a light yellow powder by carrying out the same operation as in Example 2-1 except that sodium hydride (NaH) (purity: 60.2 mass %, 286 mg, 7.17 mmol, 2.2 equivalents) was used in place of NaOMe. Isolated yield: 85.9%.

The results of Examples 2-1 to 2-6 are summarized in Table 2 below.

TABLE 2

| Example | Primary Alcohol | Base/Base Equivalent | Isolated Yield |
|---|---|---|---|
| 2-1 | 3-methoxy-1-butanol | NaOMe | 84.6% |
| 2-2 | 3-methoxy-1-butanol | DBU | 87.4% |
| 2-3 | 3-methoxy-1-butanol | NaOH | 65.7% |
| 2-4 | 3-methoxy-1-butanol | NaOEt | 85.6% |
| 2-5 | 3-methoxy-1-butanol | NaO$^t$Bu | 81.9% |
| 2-6 | 3-methoxy-1-butanol | NaH | 85.9% |

As seen from Table 2, Ru-MACHO ($1^B$-1) as a kind of ruthenium complex ($1^A$) of the present invention was obtained as a single isomer in good yield by treating $4^B$-1 as a kind of ruthenium dinuclear complex ($4^A$) with a primary alcohol and a base. In addition, all of by-products of this reaction could be easily removed by filtration of the reaction mixture and washing with methanol and water.

(Example 3-1) Production of {bis[2-(diphenylphos-phino)-ethyl]amine}carbonylchlorohydridoruthenium(II) (Ru-MACHO) ($1^B$-1) by Treating the crude product of dichloro{bis[2-(diphenylphosphino)ethyl]amine}ruthenium(II) dimer ($4^B$-1) with a Primary Alcohol and a Base The reaction formula is shown in the following Eq. 8.

[Chem. 23]

Eq. 8

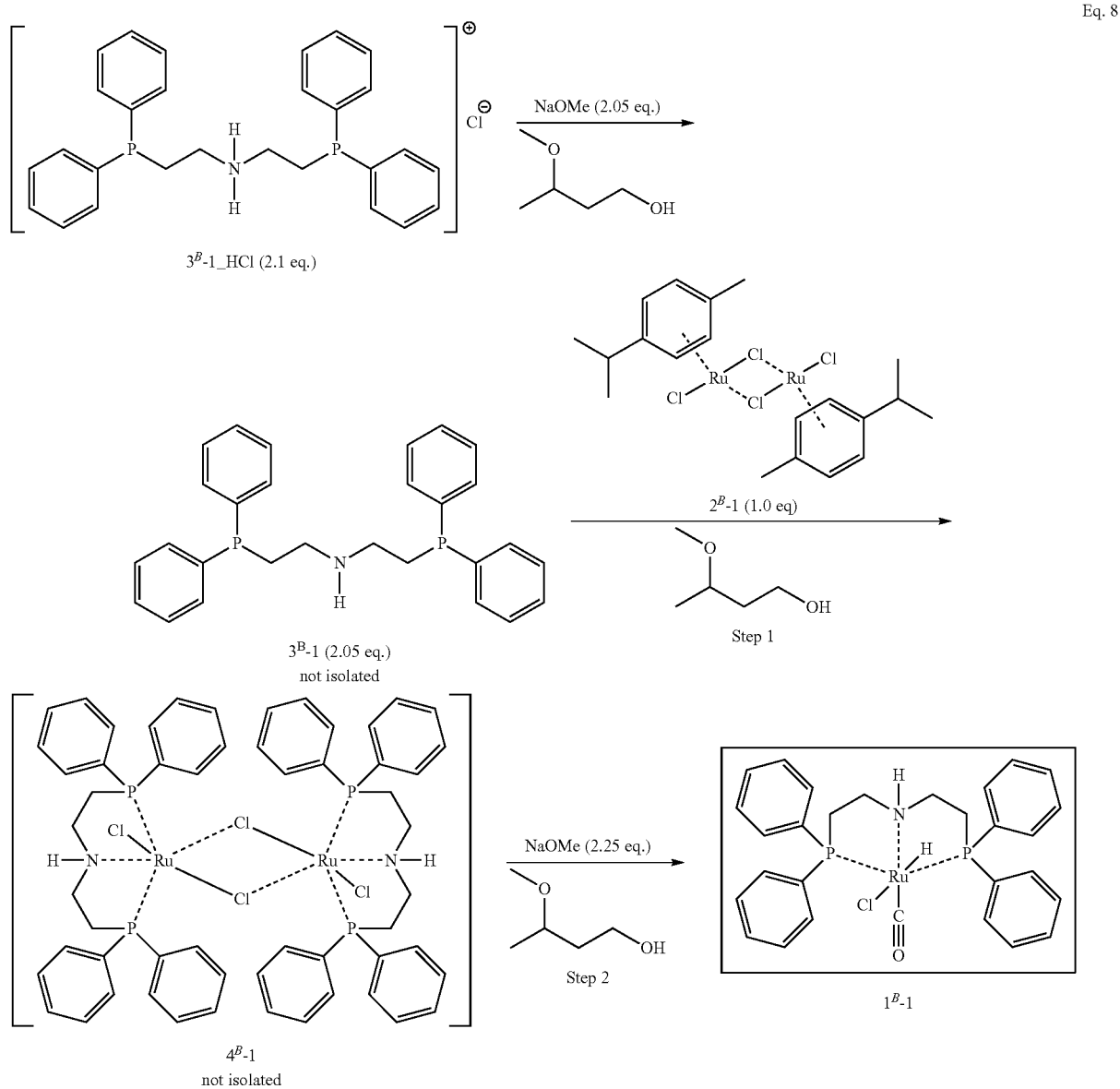

(Setup and Reaction)

A 100 mL four-necked round-bottomed flask equipped with a magnetic stirring bar, condenser, Claisen distillation apparatus, thermometer, and a three-way stopcock was evacuated and filled with nitrogen gas. Then, 3-methoxy-1-butanol (boiling point: 157° C., 60 mL), NaOMe (purity: 99.1 mass %, 730 mg, 13.39 mmol, 2.05 equivalents), and bis[2-(diphenylphosphino)ethyl]amine hydrochloride ($3^B$-1_HCl) (6.56 g, 13.71 mmol. 2.1 equivalents) were charged into the flask successively.

The obtained white suspension was stirred at room temperature for 30 minutes, and a neutralization reaction thereby proceeded while precipitating sodium chloride, and as a result, a 3-methoxy-1-butanol solution of bis[2-(diphenylphosphino)ethyl]amine ($3^B$-1) (2.05 equivalents) was obtained as a white suspension.

Dichloro(p-cymene)ruthenium(II) dimer ($2^B$-1) (4.0 g, 6.53 mmol, 1.0 equivalent) was added to the suspension above, and the resulting red suspension was stirred under reflux for 1 hour and then cooled to room temperature to give a crude product of dichloro{bis[2-(diphenylphosphino)ethyl]amine}ruthenium(II) dimer ($4^B$-1) as an orange suspension.

NaOMe (purity: 99.1 mass %, 801 mg, 14.69 mmol, 2.25 equivalents) was added to the suspension above, and the resulting suspension was stirred under reflux for 1 hour while distilling off low-boiling-point compounds by means of the Claisen distillation apparatus.

(Post-Treatment, Isolation, and Purification)

The light brown suspension obtained after the reaction was cooled to 5° C. by using an ice-water bath and filtered by suction, and the obtained crystal was washed with methanol, water and methanol successively and dried by heating under reduced pressure to give 6.38 g of the title compound ($1^B$-1) as a light yellow powder. Isolated yield: 80.5%. The NMR measurement results of this compound were consistent with those obtained in Example 1-1.

(Example 3-2) Production of Ru-MACHO ($1^B$-1) by Using Sodium Ethoxide as a Base 6.42 g of the title compound ($1^B$-1) was obtained as a light yellow powder by carrying out the same operation as in Example 3-1 except that NaOEt (purity: 98.0 mass %, 930 mg, 13.39 mmol, 2.05 equivalents (for neutralization of $3^B$-1_HCl)/1.02 g, 14.69 mmol, 2.25 equivalents (for production of $1^B$-1)) was used in place of NaOMe. Isolated yield: 81.0%.

(Example 3-3) Production of Ru-MACHO ($1^B$-1) by Using Sodium Tert-Butoxide as a Base 6.56 g of the title compound ($1^B$-1) was obtained as a light yellow powder by carrying out the same operation as in Example 3-1 except that NaO$^t$Bu (purity: 99.1 mass %, 1.30 g, 13.39 mmol, 2.05 equivalents (for neutralization of $3^B$-1_HCl))/1.42 g, 14.69 mmol, 2.25 equivalents (for production of $1^B$-1)) was used in place of NaOMe. Isolated yield: 82.7%.

The results of Examples 3-1 to 3-3 are summarized in Table 3 below.

TABLE 3

| Example | Primary Alcohol | Base | Isolated Yield |
|---|---|---|---|
| 3-1 | 3-methoxy-1-butanol | NaOMe | 80.5% |
| 3-2 | 3-methoxy-1-butanol | NaOEt | 81.0% |
| 3-3 | 3-methoxy-1-butanol | NaO$^t$Bu | 82.7% |

As seen from Table 3, Ru-MACHO ($1^B$-1) as a kind of ruthenium complex ($1^A$) of the present invention was obtained as a single isomer in good yield by treating $4^B$-1 as a kind of ruthenium dinuclear complex ($4^A$), which was not purified and isolated, with a primary alcohol and a base. In addition, all of by-products of this reaction could be easily removed by filtration of the reaction mixture and washing with methanol and water.

(Example 4) Production of {bis[2-(dicyclohexyl-phosphino)-ethyl] amine}carbonylchlorohydridoruthenium(II) ($1^B$-2)

The reaction formula is shown in the following Eq. 9.

[Chem. 24]

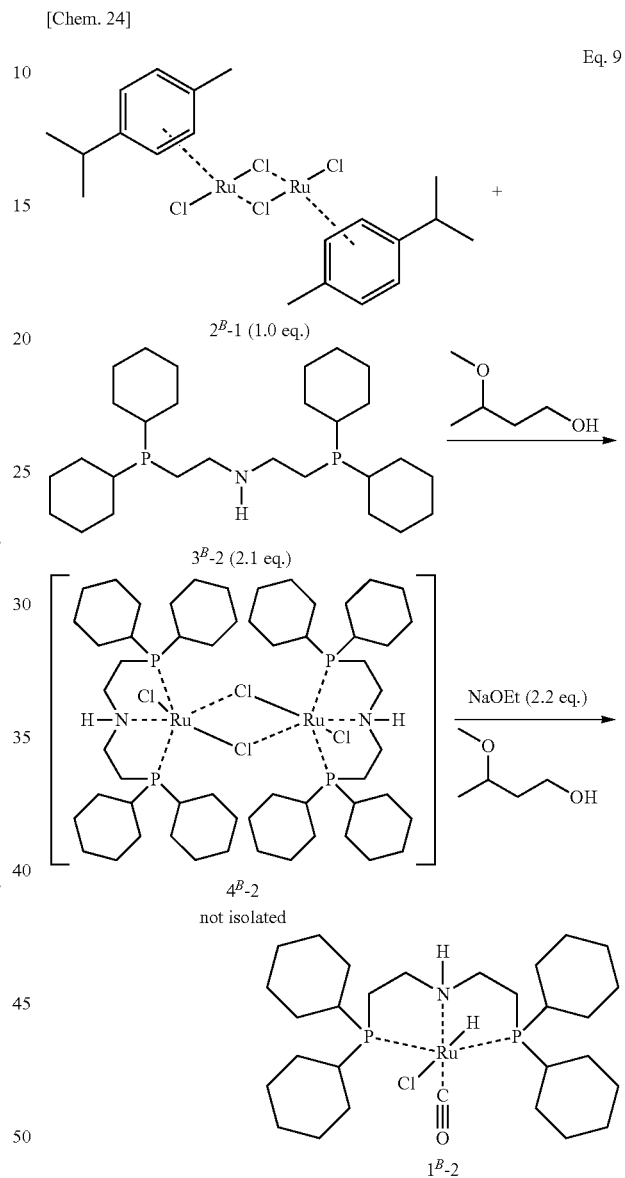

(Setup and Reaction)

A 50 mL four-necked round-bottomed flask equipped with a magnetic stirring bar, condenser, Claisen distillation apparatus, thermometer, and a three-way stopcock was evacuated and filled with nitrogen gas. Then, 3-methoxy-1-butanol (boiling point: 157° C., 20 mL), dichloro(p-cymene)ruthenium(II) dimer ($2^B$-1) (1.0 g, 1.63 mmol, 1.0 equivalent), and bis[(2-dicyclohexylphosphino)ethyl]amine ($3^B$-2) (1.59 g, 3.42 mmol, 2.1 equivalents) were charged into the flask successively.

The obtained red suspension was stirred under reflux for 1 hour and then cooled to room temperature to obtain a crude product of dichloro{bis[2-(dicyclohexylphosphino)ethyl] amine}ruthenium(II) dimer ($4^B$-2) as a red-orange suspension. NaOEt (249 mg, 3.59 mmol, 2.2 equivalents) was added to the suspension above, and the resulting suspension was stirred under reflux for 1 hour while distilling off low-boiling-point compounds by means of the Claisen distillation apparatus.

(Post-Treatment, Isolation, and Purification)

The light brown suspension obtained after the reaction was cooled to 5° C. by using an ice-water bath and filtered by suction, and the obtained crystal was washed with methanol, water and methanol successively and dried by heating under reduced pressure to give 1.60 g of the title compound ($1^B$-2) as an off-white powder. Isolated yield: 77.8%.

$^1$H NMR (400 MHz, CD$_2$Cl$_2$): δ=3.42 (t, J=12.0 Hz, 1H), 3.28-3.12 (m, 2H), 2.42-2.16 (m, 8H), 2.04-1.18 (m, 42H), −16.38 (t, J=18.4 Hz, 1H).

$^{31}$P NMR (161 MHz, CD$_2$Cl$_2$): δ=65.2 (d, J=15.9 Hz, 2P).

Also in this case, a corresponding coordination isomer was not observed at all in the NMR analysis.

It was found from the results of Example 4 that even when bis[(2-dicyclohexylphosphino)ethyl]amine ($3^B$-2) is used in place of bis[2-(diphenylphosphino)ethyl]amine ($3^B$-1), corresponding {bis[2-(dicyclohexylphosphino)ethyl]amine}carbonylchlorohydridoruthenium(II) ($1^B$-2) is obtained as a single isomer in good yield.

While the present invention has been described in detail and with reference to specific embodiments thereof, it will be apparent to one skilled in the art that various changes and modifications can be made therein without departing from the spirit and scope of the invention. This application is based on Japanese Patent Application No. 2015-193552 filed on Sep. 30, 2015, the entire contents of which are incorporated herein by reference. In addition, all references cited herein are incorporated by reference herein in their entirety.

INDUSTRIAL APPLICABILITY

By the production method of the present invention, in terms of atom efficiency, by-product removal and purity, the ruthenium complex ($1^A$) of the present invention useful as a catalyst for hydrogenation reaction can be produced with great efficiency, compared with the conventional production method. Accordingly, production of alcohols by hydrogenation reaction of ketones, esters and lactones, using the ruthenium complex ($1^A$) of the present invention, can also be efficiently conducted.

The invention claimed is:

1. A method for producing [bis(2-phosphinoethyl)amine]-carbonylhalohydridoruthenium (II) represented by the following formula ($1^A$), the method comprising reacting a ruthenium dinuclear complex represented by the following formula ($2^A$) with a compound represented by the following formula ($3^A$) in the presence of a primary alcohol and a base:

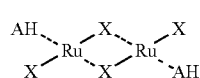

in the formula ($2^A$), the solid line represents a single bond and the broken line represents a coordinate bond; and Ru represents a divalent ruthenium ion, X represents a halide ion, and AH represents an aromatic hydrocarbon which may have a substituent,

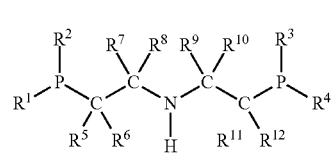

in the formula ($3^A$), the solid line represents a single bond; C represents a carbon atom, H represents a hydrogen atom, N represents a nitrogen atom, and P represents a phosphorus atom; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring,

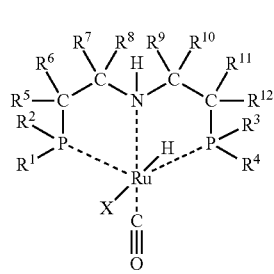

in the formula ($1^A$), the solid line represents a single bond, the triple line represents a triple bond, and the broken line represents a coordinate bond; C represents a carbon atom, H represents a hydrogen atom, N represents a nitrogen atom, O represents an oxygen atom, and P represents a phosphorus atom; Ru represents a divalent ruthenium ion and X represents a halide ion; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring.

2. The production method according to claim 1, wherein the primary alcohol is an alcohol represented by the following formula (5):

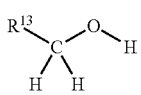

in the formula (5), the solid line represents a single bond; C represents a carbon atom, H represents a hydrogen atom, and O represents an oxygen atom; and $R^{13}$ represents a hydrogen atom or a group selected from the group consisting of an alkyl group which may have a substituent, a cycloalkyl group which may have a substituent, an alkenyl group which may have a substituent, an aryl group which may have a substituent, an oxygen-containing aliphatic heterocyclic group which may have a substituent, and an oxygen-containing heteroaryl group which may have a substituent.

3. The production method according to claim 1, wherein AH is a benzene which may have an alkyl group.

4. The production method according to claim 1, wherein X is a chloride ion.

5. The production method according to claim 1, wherein all of $R^5$, $R^6$, $R^7$, $R^8$, $R^9$, $R^{10}$, $R^{11}$ and $R^{12}$ are a hydrogen atom.

6. The production method according to claim 1, wherein each of $R^1$, $R^2$, $R^3$ and $R^4$ is independently a group selected from the group consisting of an alkyl group, a cycloalkyl group, and an aryl group which may have a substituent.

7. A method for producing [bis(2-phosphinoethyl)amine]-carbonylhalohydridoruthenium (II) represented by the following formula ($1^4$),
the method comprising treating a ruthenium dinuclear complex represented by the following formula ($4^4$) with a primary alcohol and a base:

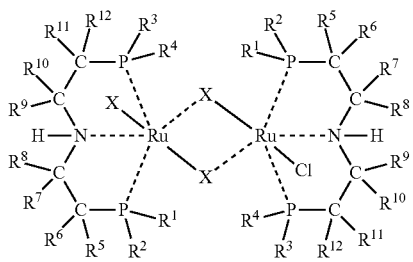

in the formula ($4^4$), the solid line represents a single bond and the broken line represents a coordinate bond; C represents a carbon atom, H represents a hydrogen atom, N represents a nitrogen atom, and P represents a phosphorus atom; Ru represents a divalent ruthenium ion and X represents a halide ion; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring,

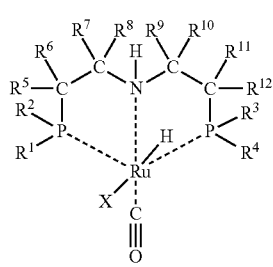

in the formula ($1^4$), the solid line represents a single bond, the triple line represents a triple bond, and the broken line represents a coordinate bond; C represents a carbon atom, H represents a hydrogen atom, N represents a nitrogen atom, O represents an oxygen atom, and P represents a phosphorus atom; Ru represents a divalent ruthenium ion and X represents a halide ion; each of $R^1$, $R^2$, $R^3$ and $R^4$ independently represents a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may be bonded to each other to form a ring which may have a substituent; $R^3$ and $R^4$ may be bonded to each other to form a ring which may have a substituent; each of $R^5$, $R^6$, $R^7$, $R^8$, $R^9$, $R^{10}$, $R^{11}$ and $R^{12}$ independently represents a hydrogen atom or a group selected from the group consisting of an alkyl group, a cycloalkyl group, an alkenyl group, an aryl group, and an aralkyl group; and each of $R^5$ to $R^{12}$ may be bonded to each other to form a ring.

8. The production method according to claim 7, wherein the primary alcohol is an alcohol represented by the following formula (5):

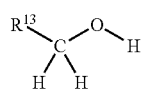

in the formula (5), the solid line represents a single bond; C represents a carbon atom, H represents a hydrogen atom, and O represents an oxygen atom; and $R^{13}$ represents a hydrogen atom or a group selected from the group consisting of an alkyl group which may have a substituent, a cycloalkyl group which may have a substituent, an alkenyl group which may have a substituent, an aryl group which may have a substituent, an oxygen-containing aliphatic heterocyclic group which may have a substituent, and an oxygen-containing heteroaryl group which may have a substituent.

9. The production method according to claim 7, wherein X is a chloride ion.

10. The production method according to claim 7 wherein all of $R^5$, $R^6$, $R^7$, $R^8$, $R^9$, $R^{10}$, $R^{11}$ and $R^{12}$ are a hydrogen atom.

11. The production method according to claim 7, wherein each of $R^1$, $R^2$, $R^3$ and $R^4$ is independently a group selected from the group consisting of an alkyl group, a cycloalkyl group, and an aryl group which may have a substituent.

* * * * *